(12) United States Patent
Zadeh

(10) Patent No.: US 10,064,707 B2
(45) Date of Patent: Sep. 4, 2018

(54) SELF-OSTEOTOMIZING BONE IMPLANT AND RELATED METHOD

(71) Applicant: Parsa T. Zadeh, Beverly Hills, CA (US)

(72) Inventor: Parsa T. Zadeh, Beverly Hills, CA (US)

( * ) Notice: Subject to any disclaimer, the term of this patent is extended or adjusted under 35 U.S.C. 154(b) by 517 days.

(21) Appl. No.: 14/335,398

(22) Filed: Jul. 18, 2014

(65) Prior Publication Data

US 2014/0329202 A1    Nov. 6, 2014

Related U.S. Application Data

(63) Continuation-in-part of application No. 13/946,509, filed on Jul. 19, 2013, now abandoned, which is a continuation-in-part of application No. 13/553,678, filed on Jul. 19, 2012, now abandoned.

(60) Provisional application No. 61/510,009, filed on Jul. 20, 2011.

(51) Int. Cl.
  *A61C 8/00*    (2006.01)
  *A61B 17/86*   (2006.01)

(52) U.S. Cl.
  CPC .......... *A61C 8/0025* (2013.01); *A61B 17/863* (2013.01); *A61C 8/006* (2013.01); *A61C 8/0022* (2013.01); *A61C 8/0024* (2013.01); *A61C 8/0068* (2013.01); *A61C 8/0069* (2013.01)

(58) Field of Classification Search
  CPC ..... A61C 8/0022–8/0025; A61C 8/006; A61C 8/0068; A61C 8/0069; A61B 17/863
  USPC .................................................. 433/172–176
  See application file for complete search history.

(56) References Cited

U.S. PATENT DOCUMENTS

| | | | |
|---|---|---|---|
| 422,307 A | 2/1890 | Libbey | |
| 3,672,058 A | 6/1972 | Nikoghossian | |
| 4,406,623 A * | 9/1983 | Grafelmann | A61C 8/0022 433/174 |
| 4,468,200 A | 8/1984 | Munch | |
| 4,846,683 A | 7/1989 | Lazzara et al. | |
| 4,863,383 A * | 9/1989 | Grafelmann | A61B 17/8625 433/174 |
| 4,961,740 A | 10/1990 | Ray et al. | |
| 5,088,926 A | 2/1992 | Lang | |
| 6,048,204 A * | 4/2000 | Klardie | A61C 8/0022 433/174 |
| 6,068,632 A | 5/2000 | Carchidi et al. | |

(Continued)

FOREIGN PATENT DOCUMENTS

| | | |
|---|---|---|
| DE | 10236125 A1 | 2/2004 |
| DE | 102009050049 A1 | 4/2011 |

OTHER PUBLICATIONS

U.S. Appl. No. 13/553,678, Zadeh, filed Jul. 19, 2012.

(Continued)

*Primary Examiner* — Matthew Nelson
(74) *Attorney, Agent, or Firm* — Susan L. McCain; Sergio Becerra; Hankin Patent Law, APC

(57) ABSTRACT

A bone implant includes a head and a core body extending from the head to a tip. An osteotomy blade extends outwardly from at least a portion of the core body to form a spiral thread. Channels form bone cutting edges of the implant. The implant, and particularly the osteotomy blade, is configured to self-osteotomize and direct cut bone into the channels to facilitate bone growth and grafting and integration of the implant to the bone.

26 Claims, 23 Drawing Sheets

(56) References Cited

U.S. PATENT DOCUMENTS

| | | | |
|---|---|---|---|
| 6,099,312 A | 8/2000 | Alvaro | |
| 6,273,722 B1* | 8/2001 | Phillips | A61C 8/0018 433/173 |
| 6,315,564 B1 | 11/2001 | Levisman | |
| 6,663,388 B1 | 12/2003 | Schar et al. | |
| 6,679,701 B1 | 1/2004 | Blacklock | |
| 7,608,105 B2* | 10/2009 | Pavlov | A61B 17/862 623/17.11 |
| 7,806,693 B2 | 10/2010 | Hurson | |
| 7,854,316 B2 | 12/2010 | Park et al. | |
| 8,221,119 B1 | 7/2012 | Valen | |
| 8,337,205 B2 | 12/2012 | Reed | |
| 2004/0091837 A1 | 5/2004 | Horiuchi | |
| 2004/0197741 A1* | 10/2004 | Mopper | A61C 3/02 433/226 |
| 2006/0216672 A1* | 9/2006 | Dinkelacker | A61C 8/0018 433/173 |
| 2007/0020582 A1* | 1/2007 | Neumeyer | A61C 8/005 433/173 |
| 2007/0099153 A1 | 5/2007 | Fromovich | |
| 2007/0202464 A1* | 8/2007 | Schwarz | A61C 8/0012 433/173 |
| 2007/0274795 A1* | 11/2007 | Cirino | B23B 51/02 408/233 |
| 2008/0152445 A1* | 6/2008 | Jensen | B23D 77/006 408/145 |
| 2008/0153064 A1* | 6/2008 | Han | A61C 8/0022 433/174 |
| 2008/0241791 A1 | 10/2008 | Bulard et al. | |
| 2008/0261175 A1 | 10/2008 | Hurson | |
| 2008/0280255 A1* | 11/2008 | D'Alise | A61C 8/0025 433/174 |
| 2008/0286720 A1 | 11/2008 | Reed | |
| 2009/0258328 A1* | 10/2009 | Chen | A61C 8/0018 433/173 |
| 2010/0009316 A1* | 1/2010 | Hurson | A61C 8/0018 433/173 |
| 2010/0055645 A1* | 3/2010 | Mullaly | A61C 8/0025 433/174 |
| 2010/0092920 A1 | 4/2010 | Hsieh | |
| 2010/0203477 A1 | 8/2010 | Crudo | |
| 2010/0209200 A1* | 8/2010 | Delacretaz | A61C 3/02 407/54 |
| 2010/0240010 A1* | 9/2010 | Holmstrom | A61C 8/0022 433/174 |
| 2010/0261141 A1* | 10/2010 | Ajlouni | A61C 8/0022 433/174 |
| 2011/0053115 A1 | 3/2011 | Gieselmann et al. | |
| 2011/0081626 A1* | 4/2011 | Hurson | A61C 8/0022 433/174 |
| 2011/0111369 A1* | 5/2011 | Laster | A61B 17/0401 433/174 |
| 2011/0117522 A1 | 5/2011 | Verma et al. | |
| 2011/0200969 A1* | 8/2011 | Schroering | A61C 8/0018 433/174 |
| 2011/0250564 A1* | 10/2011 | Hung | A61C 8/0018 433/174 |
| 2011/0294094 A1* | 12/2011 | Moshavi | A61C 8/0018 433/174 |
| 2012/0015325 A1* | 1/2012 | Chen | A61C 8/0037 433/174 |
| 2012/0178048 A1* | 7/2012 | Cottrell | A61C 8/0025 433/174 |
| 2013/0011811 A1* | 1/2013 | Gourlaouen-Preissler | A61C 8/0012 433/173 |
| 2013/0022942 A1 | 1/2013 | Zadeh | |
| 2013/0224687 A1* | 8/2013 | Karmon | A61C 8/0022 433/174 |
| 2014/0023990 A1 | 1/2014 | Zadeh | |

OTHER PUBLICATIONS

U.S. Appl. No. 13/946,509, Zadeh, filed Jan. 23, 2014.

Non-Final Office Action for U.S. Appl. No. 13/553,678 dated Sep. 17, 2013.

Non-Final Office Action for U.S. Appl. No. 13/946,509 dated Apr. 1, 2014.

International Search Report and Written Opinion for related PCT application PCT/US12/47718 dated Oct. 22, 2012.

International Preliminary Report on Patentability for related PCT application PCT/US12/47718 dated Jan. 21, 2014.

International Search Report and Written Opinion for related PCT application PCT/US13/51348 dated Oct. 29, 2013.

International Preliminary Report on Patentability for related PCT application PCT/US13/51348 dated Jan. 20, 2015.

International Search Report and Written Opinion for related PCT application PCT/US14/47267 dated Nov. 6, 2014.

International Preliminary Report on Patentability for related PCT application PCT/US14/47267 dated Jan. 19, 2016.

* cited by examiner

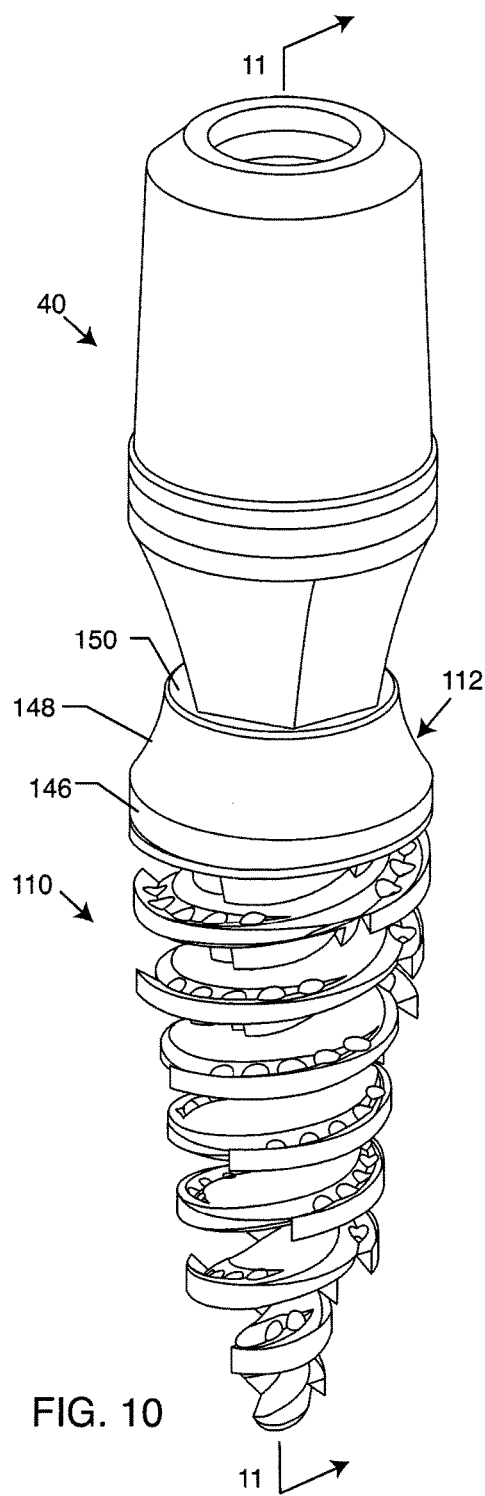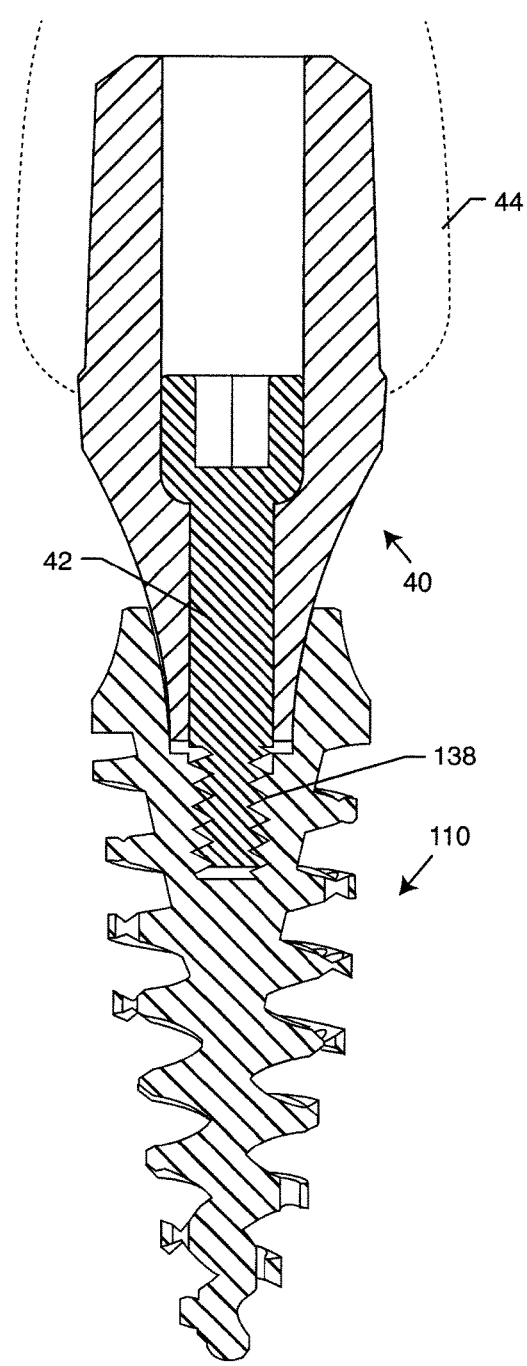
FIG. 10
FIG. 11

SELF-OSTEOTOMIZING BONE IMPLANT AND RELATED METHOD

RELATED APPLICATION

This application is a continuation-in-part of U.S. patent application Ser. No. 13/946,509, filed Jul. 19, 2013, which is a continuation-in-part of U.S. patent application Ser. No. 13/553,678, filed Jul. 19, 2012, which claims priority to U.S. Provisional Application No. 61/510,009, filed Jul. 20, 2011.

BACKGROUND OF THE INVENTION

The present invention generally relates to bone implants, such as dental implants. More particularly, the present invention is directed to a self-osteotomizing and self-grafting bone implant which creates its own osteotomy and facilitates bone growth and integration of the implant.

Traditionally, orthopedic medicine and dentistry have copied older established industries, like carpenters, to create fasteners for prosthetic items to be attached directly to bone in the form of various cone screws. In such non-medical, inanimate industries, as in cases of wood, plastic or metal, the principal of direct fasteners is based upon compressibility (wood), flexibility (plastic) or malleability (metal) or a combination of these properties being fastened to.

In all these cases, a hole is created in the receiving material slightly smaller than the selected screw or fastener for the job. The material shavings from these drillings have no cohesive or adhesive properties and are removed from the drilling site by the spiral action of the drill and discarded. The mass of the material that is removed by the drill is replaced mainly by the body of the screw or fastener.

The threads of the fastener take advantage of the three properties of compressibility, flexibility and malleability of the receiving material to engage it with large enough frictional force so as to secure the fastener to the recipient material. The ultimate tightness or securement of the fastener in non-vital objects is the same initial tightness that is achieved by the frictional forces between the body of the screw and the walls of the hole and engagement of the threads into the material. Such non-vital structures (wood, plastic, metal) are usually homogonous in nature with predictable compressibility, flexibility or malleability factors and therefore the strength and behavior of the fastener can be controlled by the various properties of the fastener body and threads.

Human bones, however, have different properties depending on their location. Each bone has different properties from outside to inside. Hip bone, spines and upper jaw are porous, whereas the lower jaw, cranium and long bones are impervious at the outer shell. They all have spongy and softer structure as their core is approached. This diverse structure of the bones from one part of the body to another and within the same area from cortex (outer layer) to medulla (inner layer), makes the bone an unpredictable material for implants and fasteners. Inconsistencies in vital bone structure have resulted in many limitations in the current procedures. This has resulted in medical professionals and medical device engineers establishing over engineering and rescuing techniques, such as placing more implants or fasteners than needed or using fasteners or implants which are wider or longer than necessary, to make their procedures as successful as possible.

Although human bones have no sensory innervations, the bones experience pain by the stretch receptors in the periosteom, the outer thin covering of the bone. Therefore, while the drilling of the bone does not contribute to post-operative pain, placement of current bone screws or implants that rely on frictional forces for their stability cause expansion of the recipient bone, resulting in the main source of post-operative pain in orthopedic and dental implant surgeries.

The limitations and unpredictable bone qualities are many times greater in dental implant surgery as the implants are placed in place of freshly extracted teeth or teeth that were previously lost, such as due to chronic infections that created voids in the bone. In current dental implant systems, the relative condensability of the bone is taken advantage of for initial implant stability. For implants supporting dental restorations, a hole is made in the bone (an osteotomy), which is slightly smaller in diameter than that of the proposed implant, by drilling at 800-1500 rotations per minute (RPM), typically with the use of saline coolant. The process usually involves creating progressively larger diameter holes which are drilled into the jawbone. Special twist drills are used in increasing the diameter until a hole of a size of 0.2-0.4 mm smaller than the implant cylinder or body is achieved.

The implant is then either tapped into this hole or more commonly "screwed" into the hole, much like a screw is driven into wood. Depending on the density of the recipient bone and the implant system in use, the osteotomy (hole) may be tapped before implant placement or the implants come with self-tapping features. In all these cases, the space for the implant is created mostly by drilling the native bone out and the implant is initially stabilized by condensing the immediate adjacent bone due to the implant being slightly larger than the tapped hole or osteotomy.

Creating a perfectly sized and shaped osteotomy is the greatest challenge for the implant dentist. Taking into consideration the fact that this osteotomy is performed in a physically unpredictable bone mass in the oral cavity between tongue and cheek, in a wet and bloody field with potential operator hand movement and patient movement creates many challenges for successful implant placement. Physically, jawbone in a live person varies greatly and unpredictably in density, condensability, texture and hardness from one site to another and at the same site from one mm in diameter or depth spot to the next. Live human bone is erratically fragile in small thicknesses. This fragility particularly complicates osteotomy creation in multi-rooted teeth sockets where thin webs of bone are the only anatomically correct position for the implant. All of these factors further depend on the condition and time of the extracted tooth and age of the implant recipient.

In current systems, the sequential drilling protocol removes and brings to surface any native bone that has occupied the space of the future implant. The bone shavings are often suctioned away along with the coolant liquid. Although there are commercially available "bone traps" that can be used to trap these shavings by the surgical suction mechanism, there are concerns with harvesting the bone in this manner due to potential bacterial contamination. Moreover, due to the nature of the suction mechanism, the trapped bone is repeatedly and cyclically washed and dried in the trap before it is recovered, thereby compromising the vitality and viability of the removed bone.

It can take a period of approximately three to six months after the emplacement of the body portion of the implant within the osteotomy for bone tissue to grow into the surface irregularities of the implant and secure the body portion of the implant in place within the bone bore or osteotomy. Following this three- to six-month period, an artificial tooth or other prosthetic component is typically secured to the implanted body portion, such as attaching a dental abutment to the implant. The most common cause of implant failure is the lack of initial stability, which is nothing but the inability and limitations of the system to create the perfectly sized and shaped osteotomy for the chosen implant and patient. It is important to know that the perfect size of the osteotomy for each implant size varies and depends on the condensability of the bone in that site, which can only be accurately known while the implant is being seated in the osteotomy. Inappropriate osteotomy size for a particular site is the most common cause of implant waste at dental offices that contributes to unnecessary higher cost to the consumers.

If the osteotomy size was overestimated, the primary stability suffers with risk of early mobility and implant loss in one to two weeks. If the size was underestimated, the primary stability will be excellent, but the excessive pressure at the implant bone interface, either through ischemic necrosis of the bone layer adjacent to the implant or through enzymatic activity from the pressure, causes the implant to fail in three to four weeks.

Another reason for bone necrosis and subsequent failure of dental implants is damaging the osteotomy site by overheating it during drilling. An overused, worn drill in a hard bone can generate enough heat to damage the bone to the extent that the implant does not integrate. Most implant systems recommend frequent changing of the drill sets, and others recommend "single use" drill sets to ensure sharp cutting edges every time. Needless to say, either way, there is a high per-implant cost in drilling supplies associated with the current systems.

In places where the implant is placed in thin bones, like the septum of a multi-rooted tooth, the success of current implants is limited due to the high chance of fracture of this septum either by sequential drillings or by the pressure of the implant itself.

The success of osseointegration depends on microscopically close adaptation of the vital host bone to the implant surface. The immediately placed implant by virtue of the way that it has become to be in its final position, such as by rotation, although immobile by at least a tripod of tight areas, has gaps filled with blood in its bone-implant interface. Provided that the conditions are favorable, this implant is considered "oseo-integrated" when new bone cells grow into these gaps, totally obliterating any space between the host bone and the implant. This process takes approximately two to six months and hence the typical waiting period of three to six months following implant placements for integration. If part of the implant surface is in grafted bone, other than autogenous bone, the integration time is further extended because usually the grafted material has to first get resorbed and then host bone grows into its space. Any micro or macro movement of the implant surface during this period prevents formation of bone next to its surface and results in failure.

Accordingly, there is a continuing need for an improved bone implant which will consistently result in adequate and quick anchoring of the implant to the bone, and thus implant stability. The present invention fulfills these needs, and provides other related advantages.

SUMMARY OF THE INVENTION

The present invention resides in a self-osteotomizing and self-grafting bone implant, with macro-stabilizing features, that osseointegrates within a much shorter time period. The implant generally comprises a head and a core body extending from the head to a tip. An osteotomy blade extends outwardly from at least a portion of the core body and forms a spiral thread having multiple turns around the core body to the tip. At least a portion of a surface of the osteotomy blade distal and facing generally outwardly from the core body is generally flat and defines a stabilizing wall. The stabilizing wall includes a bone cutting edge.

A cavity is formed in the implant which is adapted to receive bone fragments cut by the osteotomy blade as the implant is driven into the bone. Typically, the cavity comprises at least one channel extending a length of the implant so as to pass through multiple turns of the osteotomy blade. Usually, the at least one channel comprises multiple channels spaced apart from one another. The channels are open-faced and extend in depth from an outer edge of the thread towards the core body, and even into the core body. The at least one channel is non-rectilinear, typically spiral, and oriented a direction generally opposite the spiral thread of the osteotomy blade. The at least one channel may extend from the head to the tip of the implant. The channel may also extend into a neck of the head of the implant as well.

The open-faced channel is formed in the thread at an angle which is not normal with respect to the elongated axis of the core body. The channel is cut into the thread at an angle of less than ninety degrees, creating a positive rake angle, such as thirty degrees. This creates a bone cutting edge on one surface of the channel, while presenting a non-cutting edge at the opposite edge or surface of the channel. In essence, the channel creates multiple osteotomy blades having one or more leading bone cutting edges as the one or more channels are formed through the spiral thread of the implant.

Typically, the implant is generally tapered from the head to the tip. At least a portion of the osteotomy blade adjacent the core body is of increasing cross-sectional thickness from the head towards the tip.

The tip is rounded and corresponds to a diameter of a pilot hole drilled into the bone. Typically, the diameter of the tip is slightly smaller than that of the pilot hole.

The head of the implant may be configured to receive a dental abutment. In one embodiment, a generally cylindrical neck of the head is disposed adjacent to the core body. A generally concave outer surface of the head extends between the neck and an upper head surface. This feature encourages bone growth on top of the implant, further securing the implant in place.

In order to install an implant embodying the present invention into a bone, a pilot hole is drilled into the bone having the diameter generally that of the diameter of the tip of the implant or slightly larger. Typically, the pilot hole is drilled to a depth corresponding to a length of the in-portion of the implant. The pilot hole may be in the shape of the core of the implant. The tip of the implant is inserted into the pilot hole. The implant is drivingly rotated, causing the osteotomy blade to cut into the bone and create an osteotomy generally corresponding to a configuration of an in-bone portion of the implant. Bone fragments cut by the osteotomy blades are received into the one or more channels while the implant is rotated. Directing and receiving the cut bone fragments (fresh autogenous graft) into the channels lessens the time required to integrate the implant into the bone. Moreover, the implant is essentially carved into the bone, creating its own osteotomy, and thus non-autogenous bone material is not required for grafting.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 10 is a perspective view of a bone implant embodying the present invention having a dental abutment attached thereto;

FIG. 11 is a cross-sectional view taken generally along line 11-11;

DETAILED DESCRIPTION OF THE PREFERRED EMBODIMENTS

Figure 1:
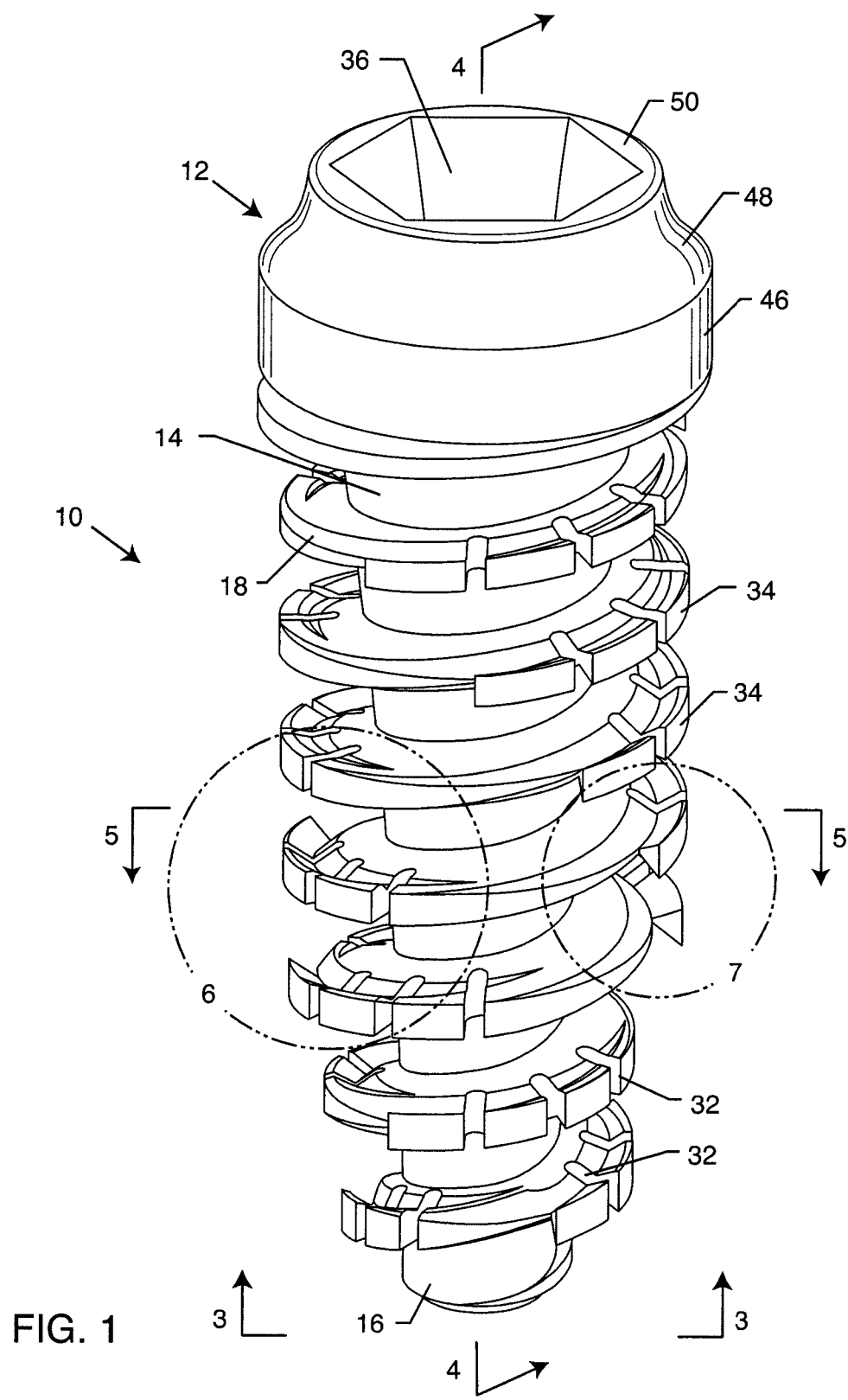
FIG. 1 is a side perspective view of a bone implant embodying the present invention.

As shown in the accompanying drawings, for purposes of illustration, the present invention resides in a self-osteotomizing and grafting implant. As will be more fully described herein, the osteotomy is achieved by the implant 10 itself as it is being driven into place. The bone shavings from the osteotomy are collected around the implant 10 as it is seated and act as autogenous bone graft, filling in the voids of the implant structure and implant bone surfaces. Moreover, the implant 10 has both vertical as well as lateral stabilization due to its design, responsible for the macro-osseointegration feature of the implant.

In existing implant designs, the bone next to the implant is condensed and crushed to achieve initial stability. In the prior art, during the initial osteotomy, the bone is brought out to the surface by the twist drills and suctioned away with the irrigating solution. Once the implant is inserted, any voids or vents within the implant space are filled with blood. The blood-filled space must first be vascularized and then osteoblastic activity must fill the volume of the void with solid bone in order for the voids to contribute to the stability of the body of the implant. Thus, it takes months for the implant to osseointegrate.

The present implant design allows the osteotomy to be made in exact and precise dimension of the implant as it is being driven into place with the bone immediate to the implant surface remaining intact, vital and uncondensed, therefore remaining fully vascularized. Since the implant of the present invention creates its own osteotomy while it is driven into place, connective tissue is not interposed between the implant and the bone. With existing implants, as the initial stability is achieved by under-sizing the osteotomy for the intended implant, due to large variations in recipient site bone quality, it is impossible to design a standardized drilling protocol for the osteotomy under-sizing in all bone types, and micro-motion often results from osteotomy-implant size mismatch, resulting in many early implant failures. However, the implant of the present invention creates the osteotomy at its own dimensions and in-bone configuration, irrespective of the bone quality around it. This provides for optimal initial stability required for osseointegration while avoiding over condensing and necrotizing of the bone immediately next to the implant surface due to excessive lateral pressure from inserting the implant in an undersized drilled osteotomy for that bone quality, as is done in the prior art. The precise approximation of vital and intact bone to the implant surface requires much less osteoblastic (bone formation) activity to take place for osseointegration to take place.

Thus, the features and design of the implant of the present invention results in an efficient and rapid osseointegration. This is referred to herein as "macro-osseointegration", which is the more rapid and efficient osseointegration of the implant. The vertical channels or apertures, and to a lesser extent the horizontal channels or space between the threads or blades, are responsible for macro-osseointegration.

With reference now to FIGS. 1-7, the bone implant 10 generally comprises an upper head portion 12 having a core body 14 extending from the head to a tip 16 generally opposite the head 12. Typically, the core body 14 tapers from the head towards the tip 16. Moreover, the tip 16 is usually rounded, but it could be sharp for orthopedic applications. When inserting the bone implant of the present invention into a bone, a small pilot hole is usually formed having a diameter of approximately equal or slightly greater in size and diameter than the rounded tip 16 of the implant 10. The rounded tip 16 is non-cutting, but allows the implant 10 to follow the initial pilot hole and leads the implant in a predetermined direction dictated by the pilot hole.

In the embodiments illustrated in FIGS. 1-18, a plurality of osteotomy blades extend outwardly from the core body 14. The osteotomy blades 18 are in essence arranged end-to-end, so as to form a spiral thread, as illustrated. It will be appreciated by those skilled in the art that the spiral thread may be continuous, but still considered formed of a plurality of osteotomy blades which are arranged end-to-end even if the osteotomy blades are not separated or distinct from one another other than their design and arrangement. Alternatively, the osteotomy blades 18 could be considered by those skilled in the art to form a single continuous spiral thread.

Figures 2, 3:
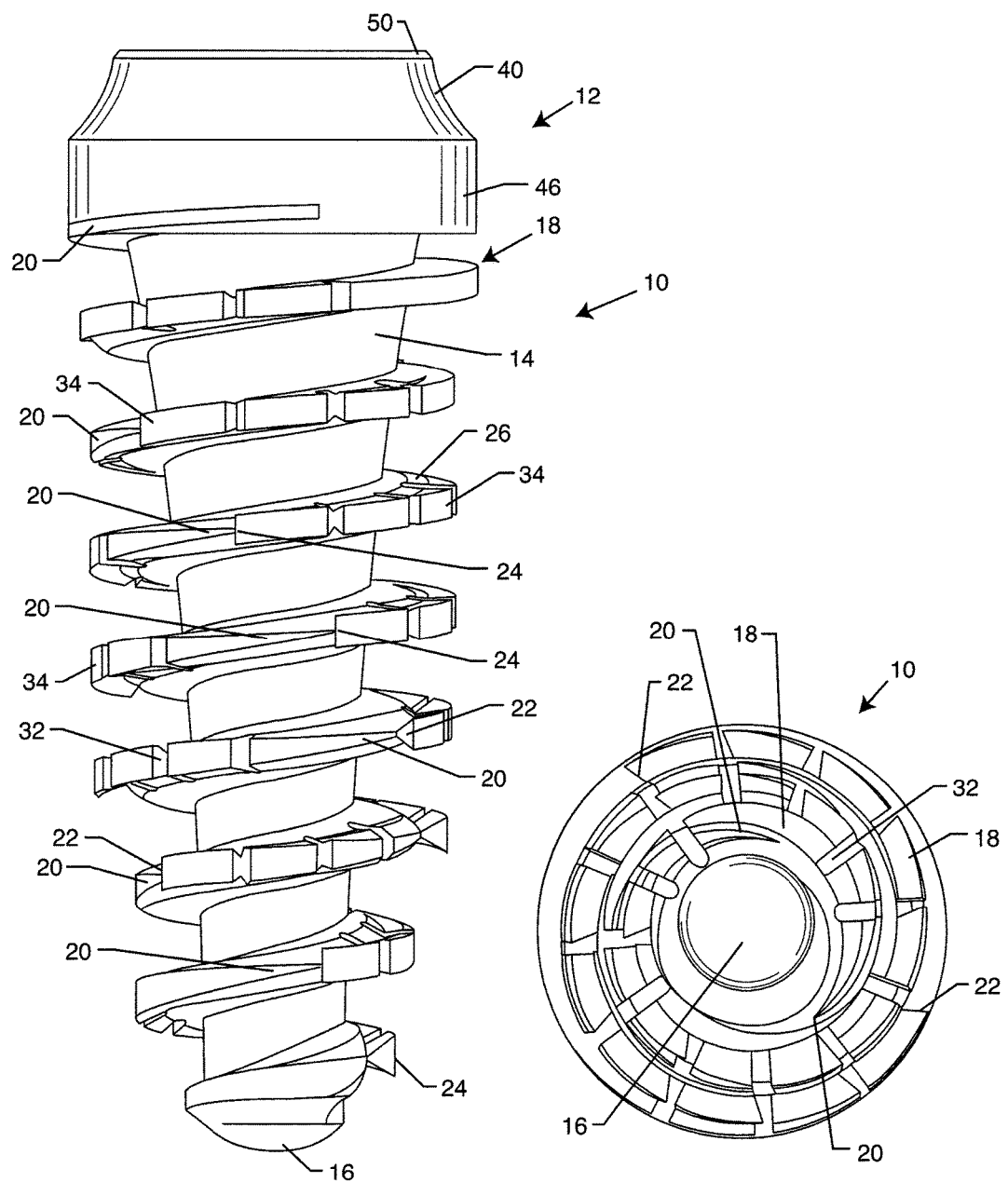
FIG. 2 is a side elevational view of the bone implant of FIG. 1.
FIG. 3 is a bottom view taken generally along line 3-3 of FIG. 1.

With specific reference to FIG. 2, in certain embodiments the osteotomy blades 18 extend all the way to the head portion 12 of the implant 10. Beginning portions of the blades 18 are referred to by the reference number 22, whereas the end portions are referred to by the reference number 20, so as to enable the reader to visualize the beginning and end of an osteotomy blade 18 as it extends and spirals around the core body 14 between the head 12 and tip 16 of the implant 10. Depending upon the application or manufacturing constraints or intended design, multiple blades 18 may form a single turn of the spiral thread, or a single blade 18 may form one or more turns of the spiral thread of the implant 10. The implant 10 may be designed and arranged such that the blades 18 closer to the head 12 are slightly larger than the blade 18 apical to it, or towards the tip 16. In this manner, the diameter of the blade 18 towards the head 12 is greater than that of the blade 18 adjacent to the tip 16, such that the overall implant 10 is tapered or conical in configuration.

In lieu of having threads, as is common in prior implants, the present invention incorporates osteotomy blades 18, which have bone-cutting peripheral edges 24. The cutting edges 24, and thus the blades 18, create the nearly exact space they will occupy in their lineal position as they get rotated or screwed into place in the bone. Typically, the cutting edges 24 face away from the core body 14.

The self-cutting nature of the bone cutting edges 24 of the osteotomy blades 18 provides more stability initially within the bone, in part due to the fact that the surrounding bone is not crushed or smeared in the placement process, as is the case when using current threaded implants. Due to this, there will be faster growth of bone, or osseointegration, around the blades 18 and implant 10.

Figures 4, 5:
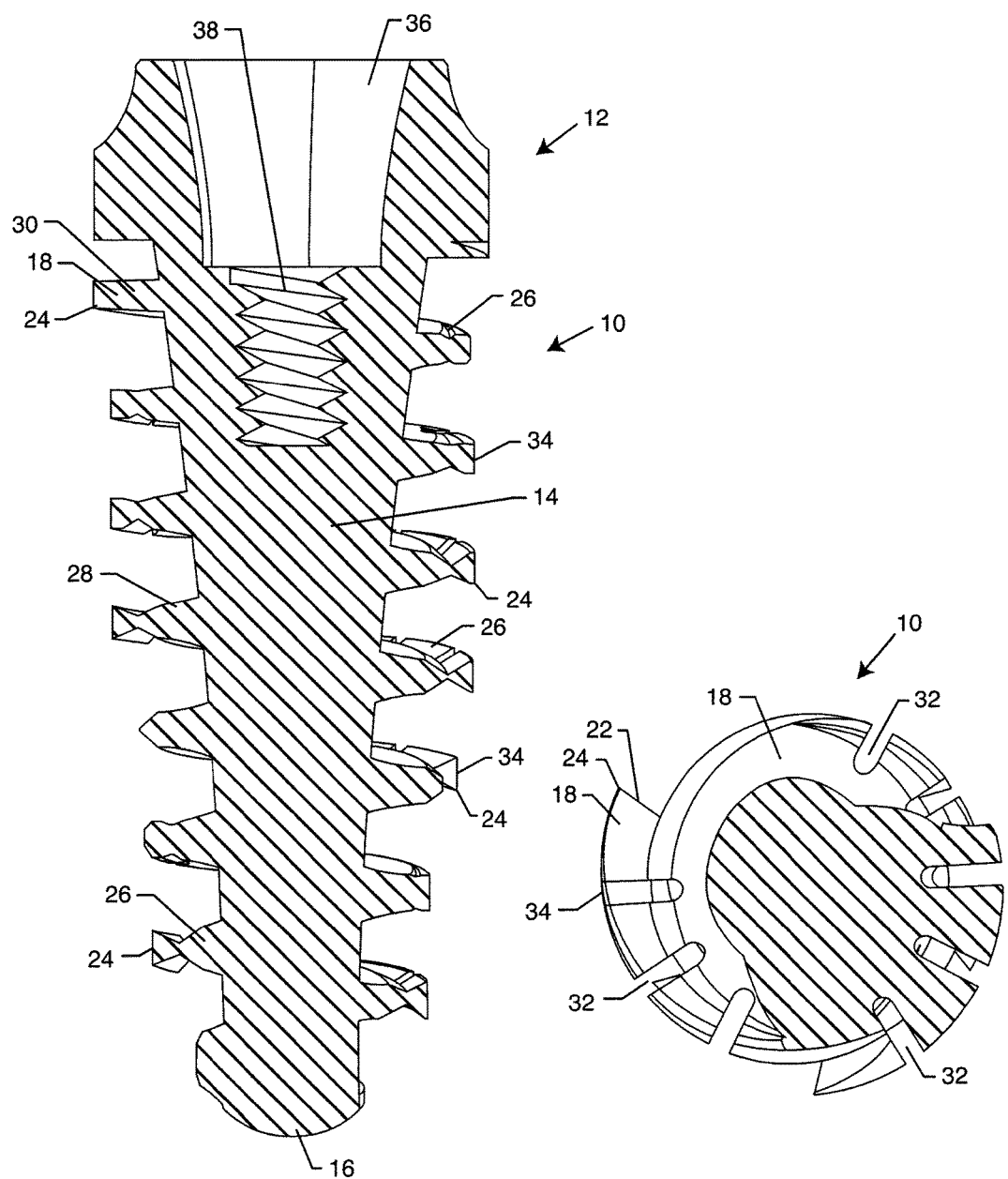
FIG. 4 is a cross-sectional view of the bone implant taken generally along line 4-4 of FIG. 1.
FIG. 5 is a partial cross-sectional view taken generally along line 5-5 of FIG. 1.
Figures 6, 7:
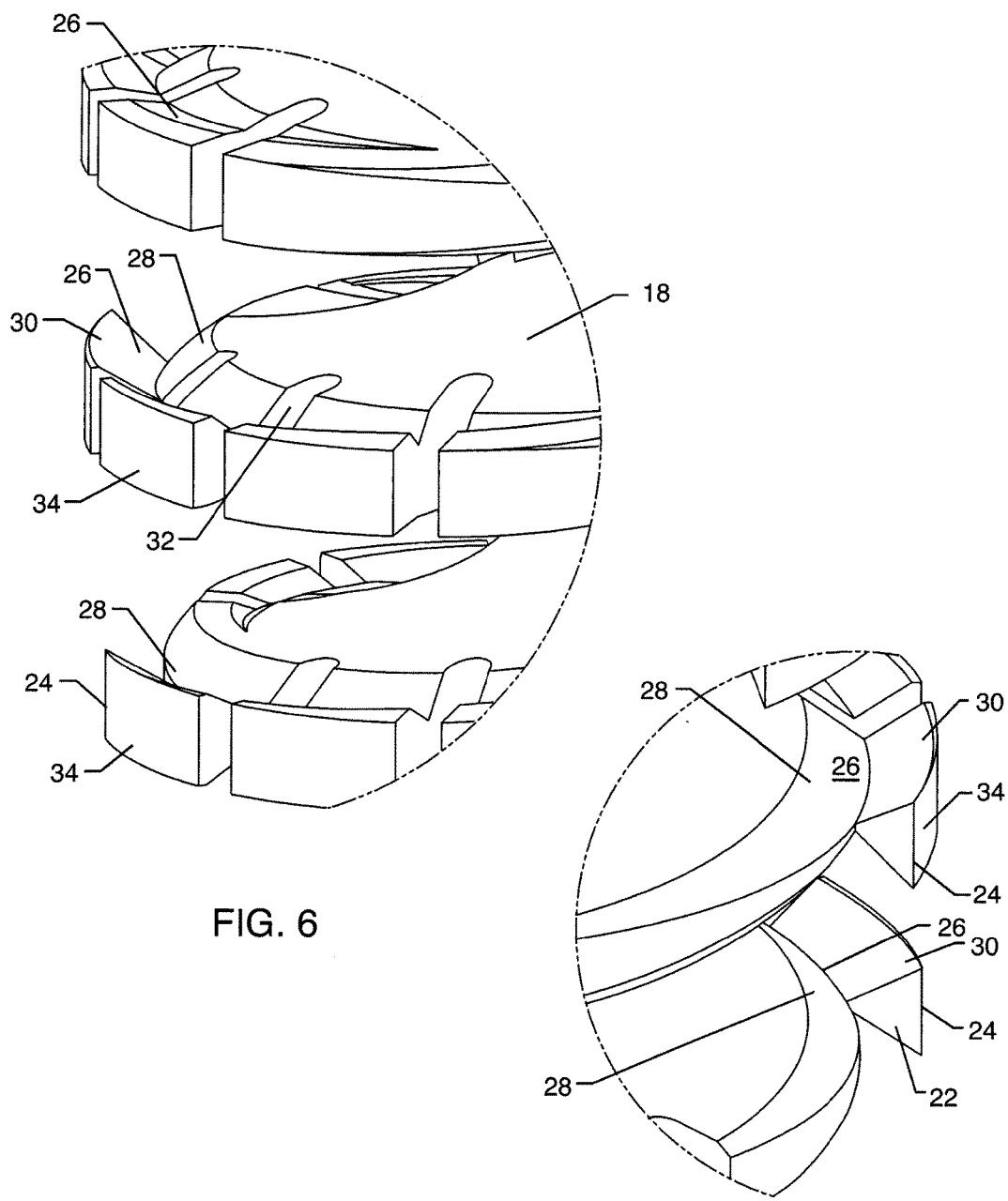
FIG. 6 is an enlarged view of area "6" of FIG. 1.
FIG. 7 is an enlarged view of area "7" of FIG. 1.

With reference now to FIGS. 4 and 6, in a particularly preferred embodiment, the thickness of the blades 18 and cutting edge 24 are greater towards the tip than the head 12. It will also be seen in FIG. 4 that the thickness of the blades 18 decreases from adjacent to the core body 14 towards their peripheral edges. This creates different thicknesses of cutting edges and blades, wherein the largest cutting edge and blade is equal to or slightly smaller than the size of the base of the smallest blade at that diameter.

With reference now to FIG. 6, at least a portion of an upper surface facing towards the head 12 and/or a lower surface facing generally towards the tip 16 may have a depression 26 which serves to collect and channel bone shavings and other material cut by the implant 10 to a space between the upper and lower surfaces of adjacent osteotomy blades 18 and into spaces 32. As can be seen in FIG. 6, the depression is generally V-shaped or U-shaped, and defined by a first angled ramp 28 of the surface of the osteotomy blade 18 extending from the core body and a second angled ramp 30 on the surface of the osteotomy blade extending generally from the peripheral outer edge or surface of the osteotomy blade towards the first angled ramp 28, so as to define and form the depression or groove 26.

The depressions 26 are usually and generally concentric with the longitudinal axis of the core body 14, however, they can also be straight lines tangential with respect to the longitudinal axis of the core body due to manufacturing limitations as well. Nonetheless, depressions 26 are formed in the blades. The depressions 26 collect the bone shavings and condenses them as they are pushed towards the end of the depression 26, which is narrower than at the opening thereof.

In one embodiment, apertures 32 are formed through the osteotomy blades 18. The apertures 32 are preferably of a size and configuration to permit blood vessels and bone to grow therein. As can be seen in the drawings, preferably the surfaces and edges formed by the apertures are generally flat or rounded so as to be non-cutting in nature so as to facilitate the growth of blood vessels therein. In the embodiment illustrated in FIGS. 1-7, the apertures are open-face and formed in the peripheral surfaces and edges of the osteotomy blades 18. Such open-face apertures are typically formed as a convenient manufacturing alternative to apertures formed completely within the osteotomy blades, such as illustrated in FIGS. 8-11. However, either arrangement will suffice provided that it facilitates growth of blood vessels and transfer of nutrients to the bone shavings and material cut by the osteotomy blades 18 during its placement and channeled by the depressions 26 towards the apertures 32 and between the adjacent osteotomy blades 18. These apertures allow blood vessels and bone to grow therein, resulting in macro-osseointegration of the implant.

Bone needs good blood supply for remodeling and healing. When the blades 18 of the implant 10 separate layers of bone from each other, circulation can suffer. This also occurs in current implant designs. The apertures 32 created through the blades 18 establish communication between layers of bone separated by the blades 18. The apertures 32, either in the form of the vertical open-faced slots or apertures along the periphery of the blades 18 or in the form of enclosed apertures 32 within the blades 18 of the implant, provide space for bone growth. This bone growth within the body of the implant provides for macro-osseointegration and substantially adds to its early stability for loading, and allows efficient and rapid osseointegration of the implant.

Furthermore, the depressions 26 formed in the blades 18 serve to collect and lead the bone shavings and cut material towards the apertures 32. This can be particularly seen in FIG. 15. In accordance with the present invention, the osteotomy shavings (live host bone tissue) is guided by the strategically placed channels and grooves in the form of depressions 26 from the cutting edges of the blades 18 towards and into the apertures 32 of the implant body. Therefore, voids are filled with live bone tissue that can readily and rapidly heal together to provide rapid stability to the inserted implant.

It will be seen that the depressions 26 vary in size and depth across their length, thus serving to channel and guide the cut bone fragments and shavings as the implant 10 is screwed into position. The collection of the bone shavings into the depression 26 and between the adjacent blades 18, in conjunction with the apertures 32 formed in the blades 18 allows blood and bodily fluid flow there in between. Eventually new blood vessels grow therein, and thus the bone shavings and cut bone material remain vital, and enhances the osseointegration of the implant 10 into the bone, creating a self-grafting feature of the implant 10. It is anticipated that the incorporation of the depressions 26, in conjunction with the apertures 32 and the self-osteotomizing blades 18, will cut the time it takes for solid bone to grow close to the implant surface and fill the voids, in order to osseointegrate, to less than half, and an anticipated three to six weeks only. Thus, it can be seen that the design of the implant of the present invention results in efficient and rapid osseointegration as compared to the prior art.

With reference now to FIGS. 1, 2, 4, 6 and 7, at least a portion, and typically the majority, of the osteotomy blades 18 have an enlarged generally flat peripheral outer surface defining a stabilizing wall 34. The stabilizing wall 34 faces generally away from the core body 14 and is generally parallel with the long axis of the implant. The generally flat peripheral outer surface defining the stabilizing wall 34 has a cutting edge 24 at its edge thereof. The incorporation of the stabilizing wall 34 at least a portion of the outer peripheral surface of the blades 18 creates immediate lateral stabilization of the implant 10 within the bone.

With reference to FIGS. 4 and 7, the incorporation of the depressions 26 as well as the stabilizing outer peripheral wall 34 along a length of the osteotomy blade 18 creates a generally triangular cross-section along at least a portion of the outer peripheral portion of the osteotomy blades 18.

Figures 8, 9:
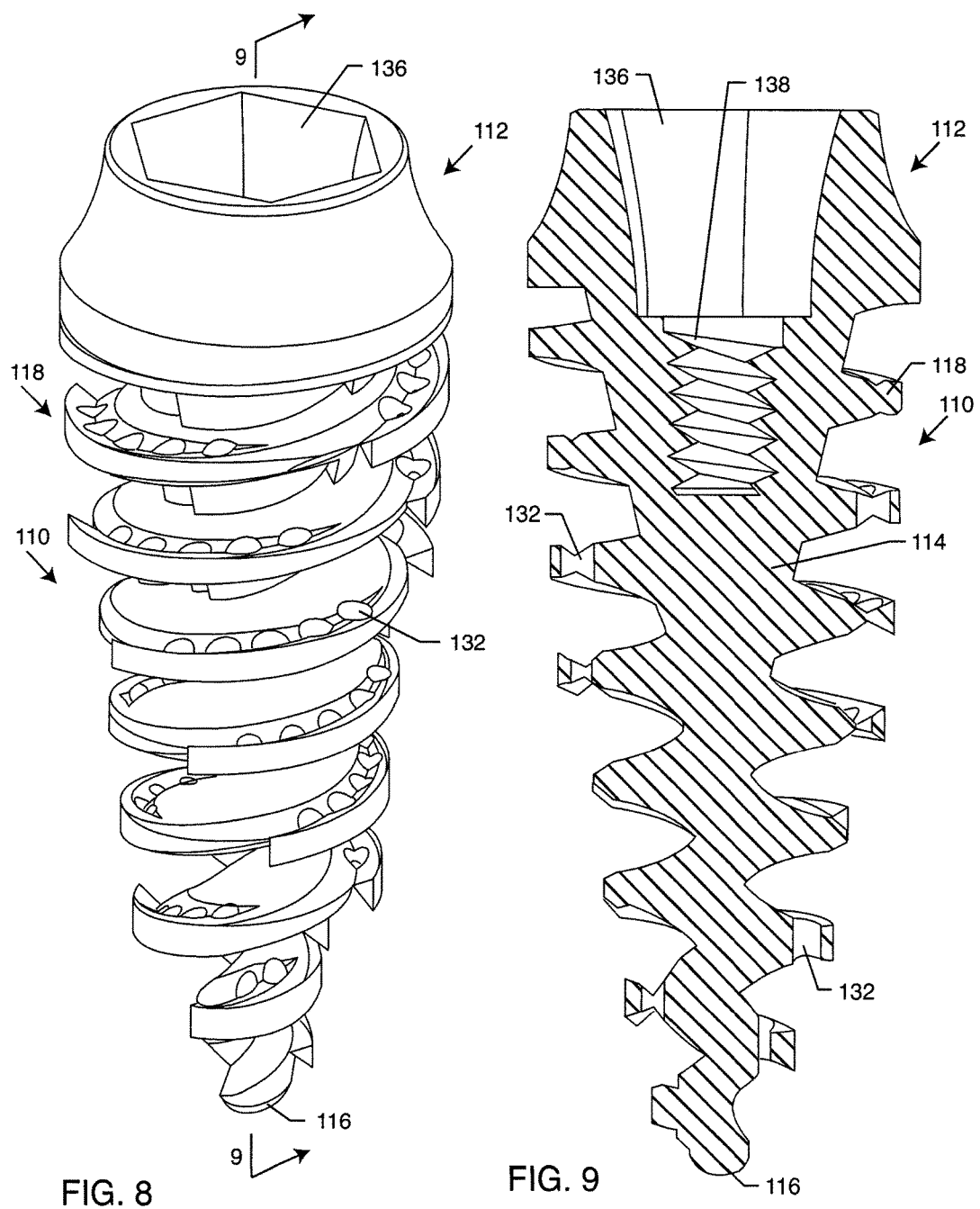
FIG. 8 is a side perspective view of another bone implant embodying the present invention.
FIG. 9 is a cross-sectional view taken generally along line 9-9 of FIG. 8.

With reference now to FIGS. 8 and 9, an implant 110 very similar to that illustrated in FIGS. 1-7 is shown, with the only differences being that the apertures 132 are formed completely within the blades 118, instead of being formed as open-face apertures. These apertures 132 perform the same functions as described above with respect to apertures 32, in that they allow bodily fluid and blood flow and blood vessel generation in the bone shavings and cut material collected in them, as well as to the segments of bone which have been cut by the osteotomy blades. It will also be noted that the core body 114 of this embodiment, as illustrated in FIG. 9, is narrower. The width of dimension of the core body 114 may be adjusted according to the type of bone into which the implant 10 or 110 is to be placed. For example, harder or softer bone may require a larger or smaller core body 14 or 114, as dictated by the need for increased or decreased diameter osteotomy blades 18 or 118. Otherwise, the embodiment illustrated in FIGS. 8-11 has the same structure and function as that described above with respect to FIGS. 1-7. Thus, all of the reference numbers in FIGS. 8-11 that pertain to the implant 110 are increased by 100, for example the head is referred to by the reference number 112 and the tip 116, whereas the head and tip are referred to by the reference numbers 12 and 16, respectively, in FIGS. 1-7.

Aside from whether the apertures 32 or 132 are formed as open-face cut into the osteotomy blades 18 or formed completely in the osteotomy blades 18, the number of blades, thickness of each blade, and the spaces between adjacent blades can be determined by the physical properties of the metallic alloy chosen for the implant, manufacturing limitations, and physiological requirements of implanted bone.

The bone implant 10 and 110 of the present invention is particularly suited for use as a dental implant. As such, the head 12 or 112 includes an internal connection 36 and 136 with internal threads 38 and 138 for an attachment of an abutment 40. Such abutments 40 are well known in the art. The abutment may be hollow, as illustrated in FIGS. 10 and 11, so as to receive a fastener 42, which engages the internal threads 38 or 138 so as to fasten the abutment 40 to the implant 10 or 110. With continuing reference to FIGS. 10 and 11, as is well known in the art, a false tooth or other prosthetic 44 is formed over the abutment 40, such as by firing ceramic material onto the abutment which mimics the patient's original tooth or teeth.

As illustrated in FIGS. 4 and 9, in a particularly preferred embodiment, the beveled internal connection is longer in the present invention for stability of the abutment 40. The longer internal bevel and shorter abutment cone connection provide stability for the abutment 40.

Figure 12:
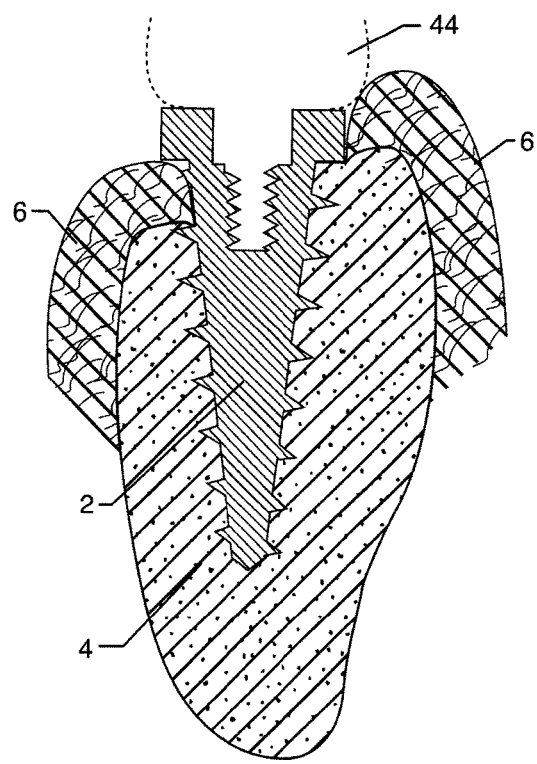
FIG. 12 is a cross-sectional and diagrammatic view of a prior art implant, with a portion thereof exposed.

With reference now to FIG. 12, a prior art implant 2 is illustrated fastened to the jawbone 4 of the patient. The alveolar crest of the underlying bone 4 is often uneven. Thus, when the original tooth is removed and a typical prior art dental implant 2 installed, the gum tissue 6 can only grow straight up on the side of the implant 2 approximately two millimeters above the bone level. In many cases, a portion of the prior art implant remains exposed, as illustrated in FIG. 12.

Figure 14:
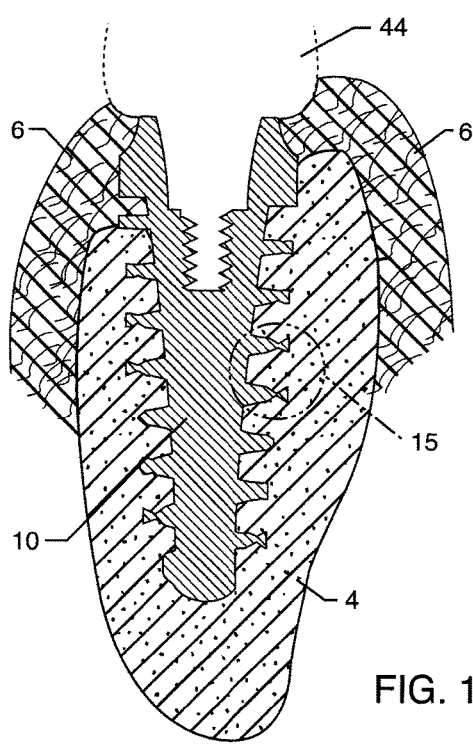
FIG. 14 is a cross-sectional and diagrammatic view similar to FIG. 13, but illustrating the implant of the present invention submerged in bone and gum tissues.

The head 12 design of the present invention overcomes this problem. The head 12 is generally comprised of a generally cylindrical neck portion 46. The portion 48 between the lower neck 46 and an upper surface 50 of the head 12 is generally cone-shaped, so as to be concave, as illustrated. Thus, the widest diameter of the neck 46 converges as a curve to the implant opening on the top surface 50. As such, the implant 10 is designed to be placed sub-crestal. This design allows taking advantage of the maximum alveolar crest bone available, as the neck 46 is circumferentially submerged in bone 4 while the top of the implant may be placed at or below the highest part of the cortical bone. This is a great advantage as it accommodates the invariable unevenness of the alveolar crest bone. Moreover, the gum tissue 6 is allowed to grow both straight up and over the neck 46 and curved portion 48, as illustrated in FIG. 14, such that there is no implant head exposure due to lack of coverage by the gum tissue 6.

Typically, the neck 46 is as wide as the upper-most blade 18. The implants may be offered in different diameters, such as narrow, regular and wide. The choice at each size depends upon the width of the alveolar crest of the area the implant is intended to be used. Thus, for example, the narrow size may be between 3-4 mm, the regular size 4-5 mm, and the wide 5-7 mm. Of course, the invention is not limited to such exact dimensions.

It will be appreciated by those skilled in the art that the implant of the present invention can be placed in locations which are otherwise not feasible with current implants and techniques. For example, sockets of freshly extracted multi-rooted teeth, where existing bone is very thin at the ideal position of the implant, the standard osteotomy can totally remove the existing bone making primary stabilization of the implant impossible.

Figure 13:
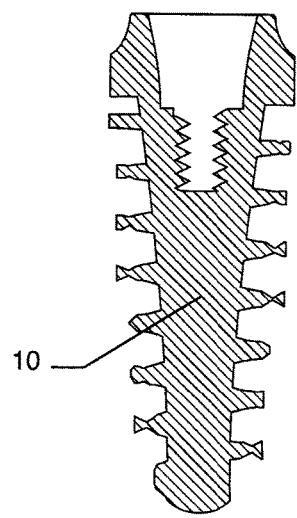
FIG. 13 is a cross-sectional diagrammatic view illustrating bone tissue having a pilot hole drilled therein for receipt of an implant embodying the present invention.
Figure 13:
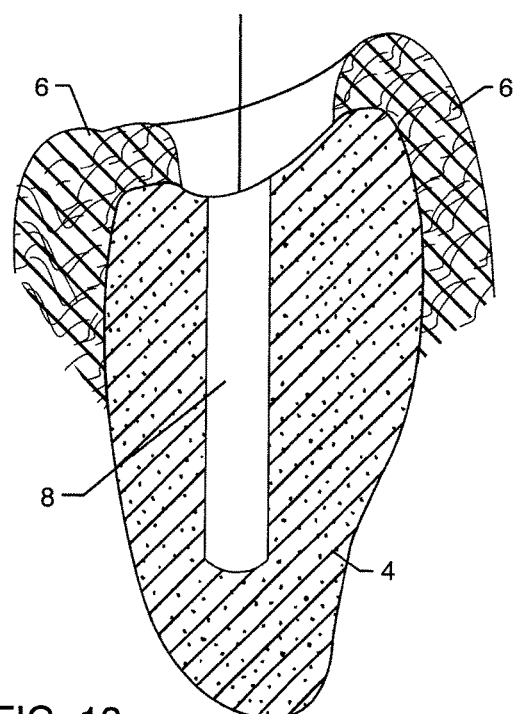
Figure 15:
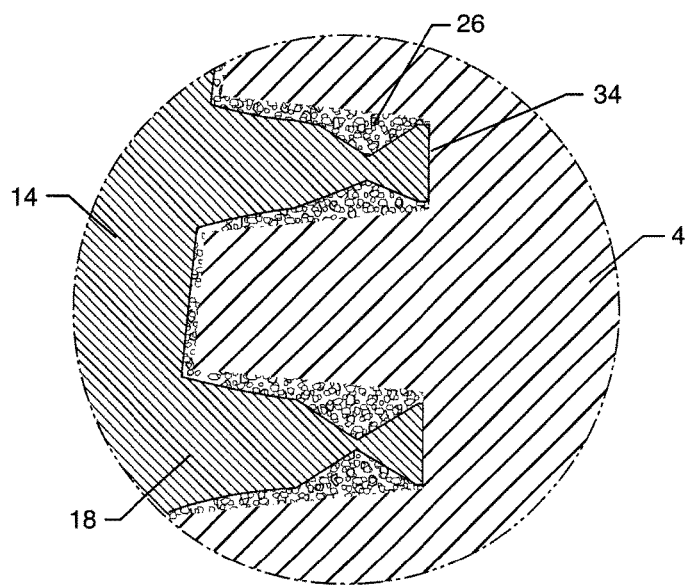
FIG. 15 is an enlarged view of area "15" of FIG. 14, illustrating channeling of bone fragments, in accordance with the present invention.

However, the implant of the present invention is only limited to the size of the pilot drill hole 8 (typically 1-2 mm) which corresponds with the diameter of the rounded tip 16 of the implant 10, as shown in FIG. 13. Thus, due to the fact that the implant 10 of the present invention is self-osteotomizing, it can be placed in sockets where prior art implants cannot be placed. Furthermore, collecting and using the bone shavings, as illustrated in FIG. 15, within the depressions 26 of the blades 18 allows the shavings to become excellent, vital autogenous bone grafts. Furthermore, the apertures 32 and 132 in the blades 18 allow collateral circulation to the bone between the blades 18 and 118.

Figure 16:
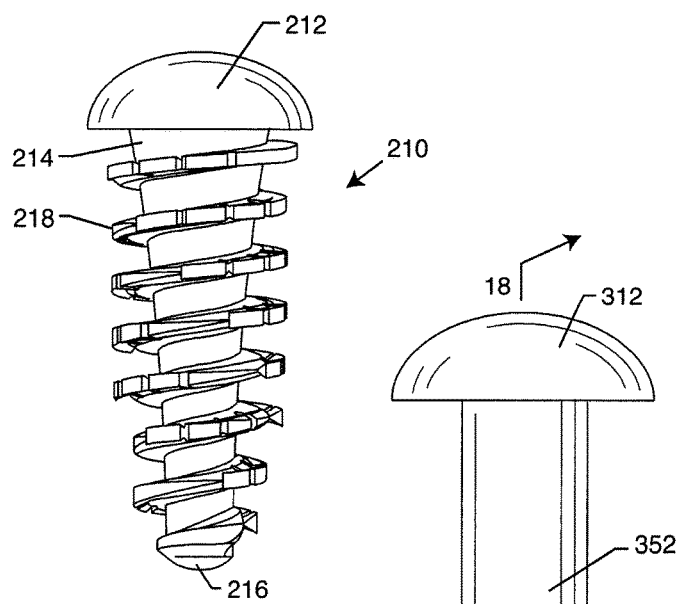
FIG. 16 is a side elevational view of another bone implant embodying the present invention.
Figure 17:
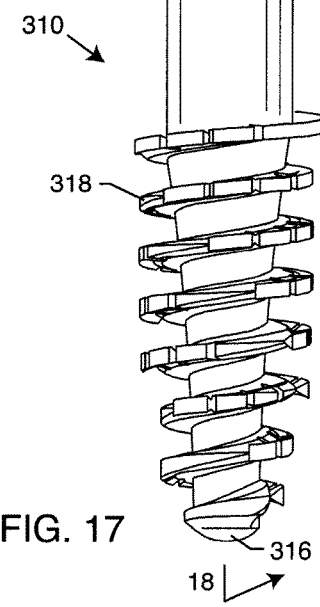
FIG. 17 is a side elevational view of yet another bone implant embodying the present invention.
Figure 18:
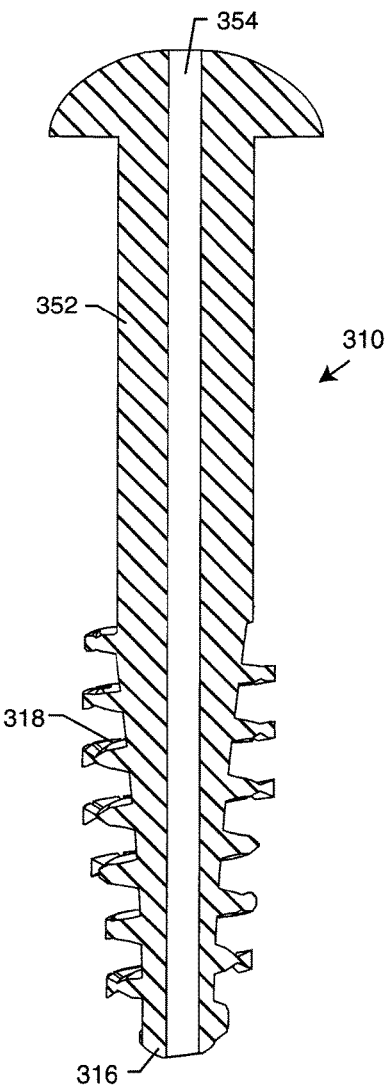
FIG. 18 is a cross-sectional view taken along line 18-18 of FIG. 17.

With reference now to FIGS. 16-18, the self-osteotomizing and grafting bone implant of the present invention is not necessarily limited to dental implants. Its features and advantages can be advantageously used in other bone implant/fastening circumstances. With particular reference to FIG. 16, a bone implant 210 or fastener is shown with a more traditional cone or flat head 212. Multiple osteotomy blades 218, having the features described above extend outwardly from a core body 214. Although the tip 216 is illustrated as being rounded, so as to be placed within a pilot hole, it is also conceived that in such instances the tip 216 could present a sharpened point so as to be driven into bone, such as during surgical operations such as those performed by orthopedists and the like, to fasten pieces of bone to one another, plates, devices and the like to bones, etc. It will be understood that the head 212 will have a slot or recess for a driver to drive the bone implant 210 into the bone.

With reference now to FIGS. 17 and 18, yet another bone implant 310 is illustrated for use in non-dental implant applications. In this case, there is an unthreaded portion 352 of the shaft between the head 312 and the tip 316. As such, the osteotomy blades 318 forming the spiral thread extend only partially along the core body 352 of the implant 310. This may be useful, for example, when attaching a plate or other device to a bone, wherein the lower portion containing the osteotomy blades 318 is inserted into the bone, and the non-threaded portion 352 extends through the plate, etc. FIG. 18 is a cross-sectional view of FIG. 16, taken generally along line 18-18, illustrating that a passageway 354 may be formed through the implant fixture 310 to serve the various purposes of the surgeon.

The non-dental applications of the bone implant of the present invention still experience the same advantages as the dental implant embodiments, in that the multiple osteotomy blades are responsible for gradual and unmatchable perfect osteotomy. The scooping feature of the individual blades due to the depressions formed within the blades preserve native bone and promote self/auto-grafting. Moreover, the apertures formed through the blades allow fluid and blood flow between adjacent sections of bone and the bone shavings, and promotes the subsequent growth of blood vessels and new bone into the apertures. The stabilizing walls formed at the peripheral end of the osteotomy blades promote horizontal or lateral stabilization, as well as vertical or lineal stabilization.

With reference now to FIGS. 19-27, another bone implant 410 embodying the present invention is illustrated. This implant 410 is similar in function to those described above. The implant 410 includes a head 412 and a core body 414 extending downwardly to a tip 416, which is typically rounded, as described above. An osteotomy blade 418 extends outwardly from the core body 414 and forms a spiral thread having multiple turns around the core body 414.

Typically the implant 410 tapers from the head 412 to the tip 416. As such, the diameter of the osteotomy blade 418 adjacent to the head 412 is generally equivalent to a neck portion 446 of the head 412, and either the osteotomy blade 418 and/or the core body 414 lessen in diameter as it progresses towards the tip 416.

Figure 19:
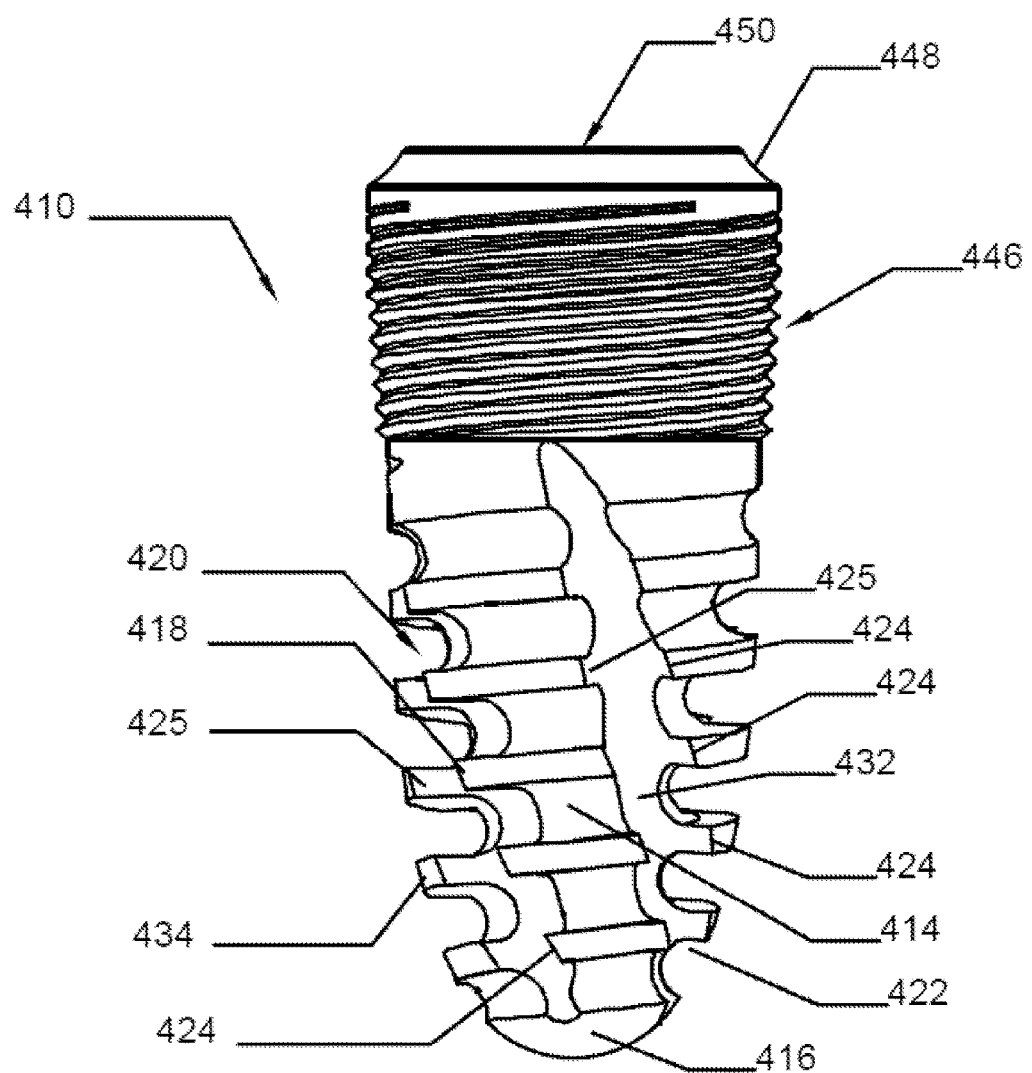
FIG. 19 is a front perspective view of a bone level implant embodying the present invention.
Figure 20:
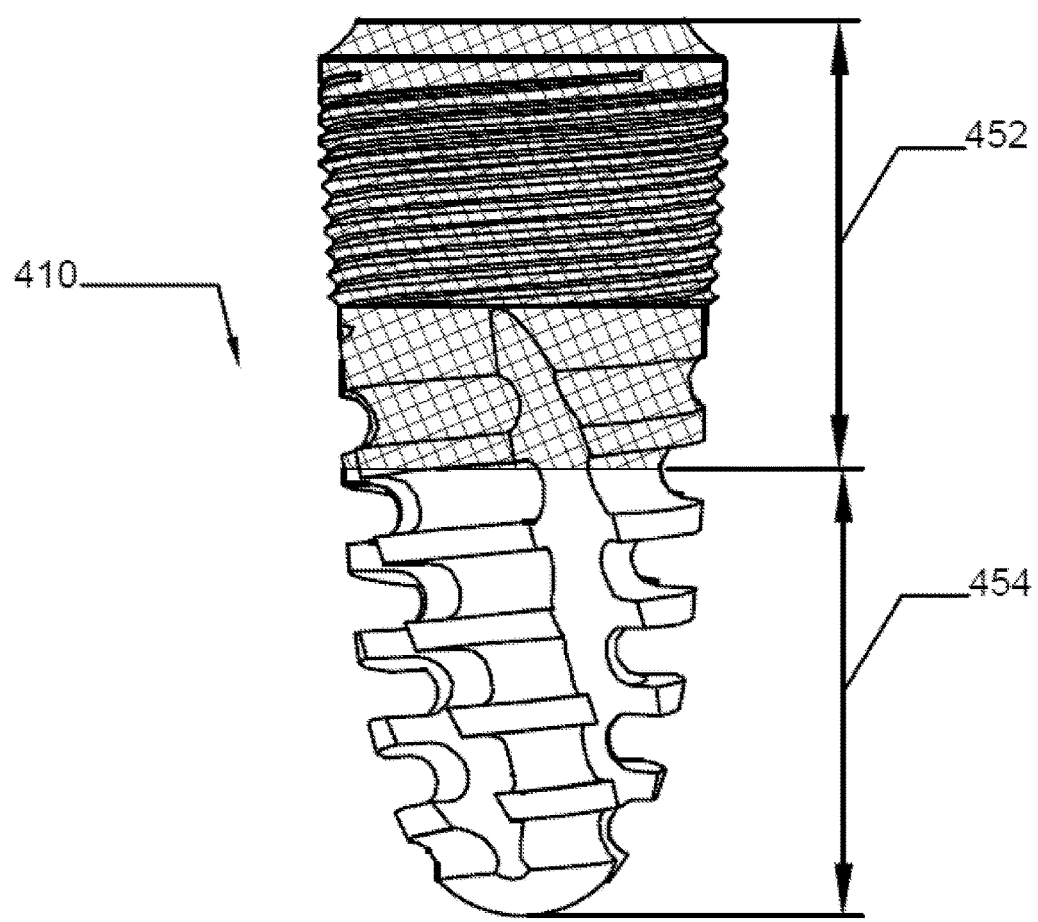
FIG. 20 is an illustration similar to FIG. 19, showing the hybrid nature of the implant with an apical portion machined finished surface for sharpness and a coronal media portion blasted surface for better osseointegration.

Instead of apertures formed exclusively within the osteotomy blade, this implant 410 includes a cavity for receiving the cut bone fragments therein as the implant 410 is drivenly rotated or screwed into the bone. In a particularly preferred embodiment, as illustrated, the implant 410 includes at least one elongated channel 432 extending a length of the implant so as to pass through multiple turns of the osteotomy blade 418. Typically, the channel 432 extends the length of the osteotomy blade spiral thread portion or an in-bone portion of the implant 410. As illustrated in FIG. 19, the implant 410 is a bone level implant, meaning that an upper surface 450 is generally at bone level, the channel 432 extends into the neck 446, such as covered by the progressively microthreaded 456 neck 446.

Figure 21:
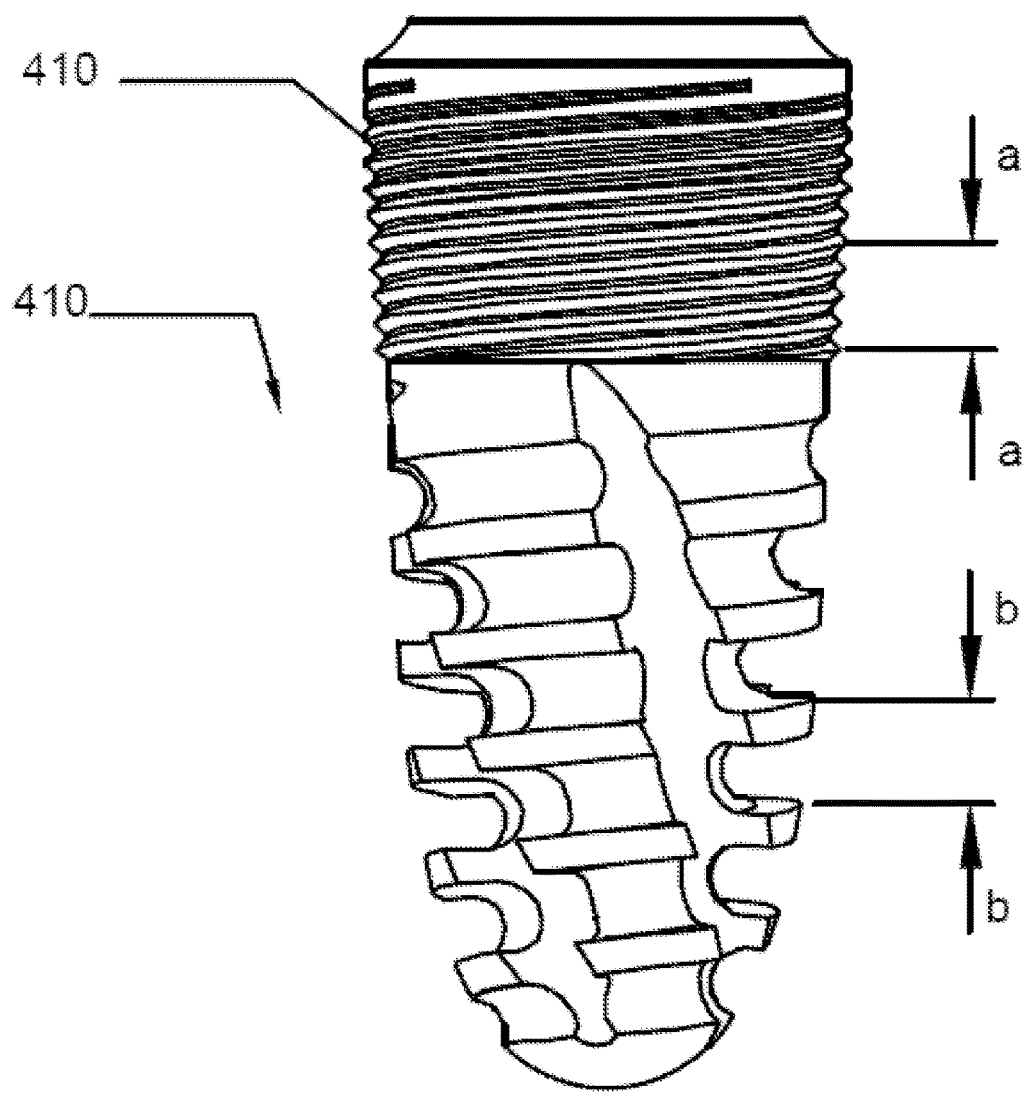
FIG. 21 is a perspective view of the implant of FIG. 19, demonstrating the equal pitch between the main cutting threads and the microthreads facilitating smooth and tension free seating of this implant.
Figure 25:
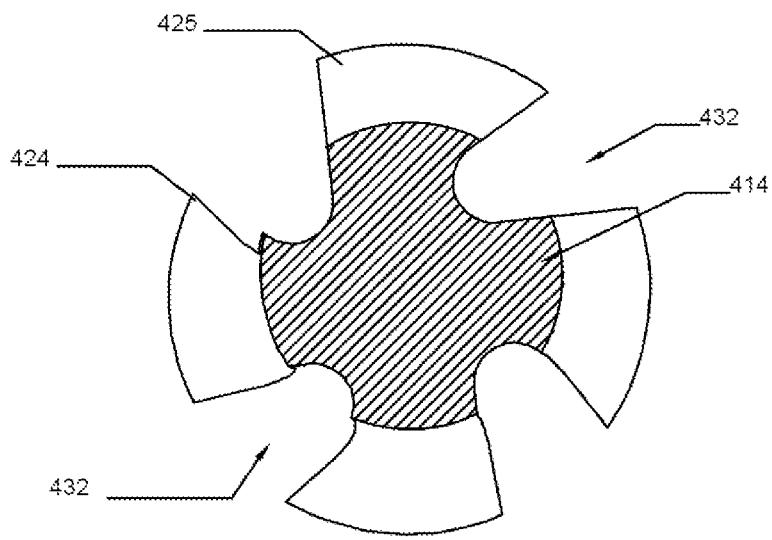
FIG. 25 is a cross sectional view taken generally along line 25-25 of FIG. 24.

The at least one channel 432 is typically open-faced, as illustrated, and extends in depth from an outer edge of the osteotomy blade thread 418 towards the core body 414, and further into the core body 414, as illustrated in FIGS. 21 and 25. This feature offers cutting capability for the core portion of the implant so that the implant would carve it's exact dimension as it is being driven in the bone. Typically, the channel is non-rectilinear, such that it forms a generally curved or spiral line from the head 412, or the uppermost portion of the osteotomy blade thread, to the tip 416 of the implant 410.

Preferably, the channel spiral or curvilinear path is oriented in a direction generally opposite the spiral pitch of the osteotomy blade 418. For example, as illustrated, the osteotomy blade thread 418 has a generally clockwise pathway, whereas the channel 432 pathway is generally counterclockwise from the head 412 to the tip 416. In this manner, as the implant 410 is rotatingly driven or screwed into the bone, the cut bone fragments and shavings will be directed into the channel 432 and channeled toward tip 416, until the one or more channels 432 are partially or fully filled with the cut bone fragments and shavings and other biological debris, until the implant 410 is fully installed in the bone. It is the formation of the one or more channels in a spiral generally having an opposite direction as the spiral thread of the osteotomy blade 418 which directs and causes the cut bone fragments, shavings, and debris to be directed into the channel 432 and moved increasingly towards the tip 416, instead of towards the head and out of the osteotomy. The continuity or continuous nature of the channels 432 from the tip 416 to the top of the spiral thread 418 facilitates the continuous channeling of cut bone fragments and shavings into the channel 432 towards the tip and until the cut bone fragments back up and essentially fill the channel from the tip 416 towards the head 412. If the channels 432 were not continuous or of a sufficient dimension the cut bone fragments and debris caused by the carving of the implant 410 into the bone would have to find other open spaces or be moved towards the top of the osteotomy and possibly exit from the top of the osteotomy and out of the patient's cut bone.

As described above, directing and receiving the cut bone fragments from the osteotomy blade 418 into cavities, such as the channel 432, greatly enhances macro-osseointegration and reduces the time needed for the implant 410 to integrate into the bone. This occurs because blood and blood vessels easily grow into these channels that are filled with fresh and vital autograft bone material.

Figure 22:
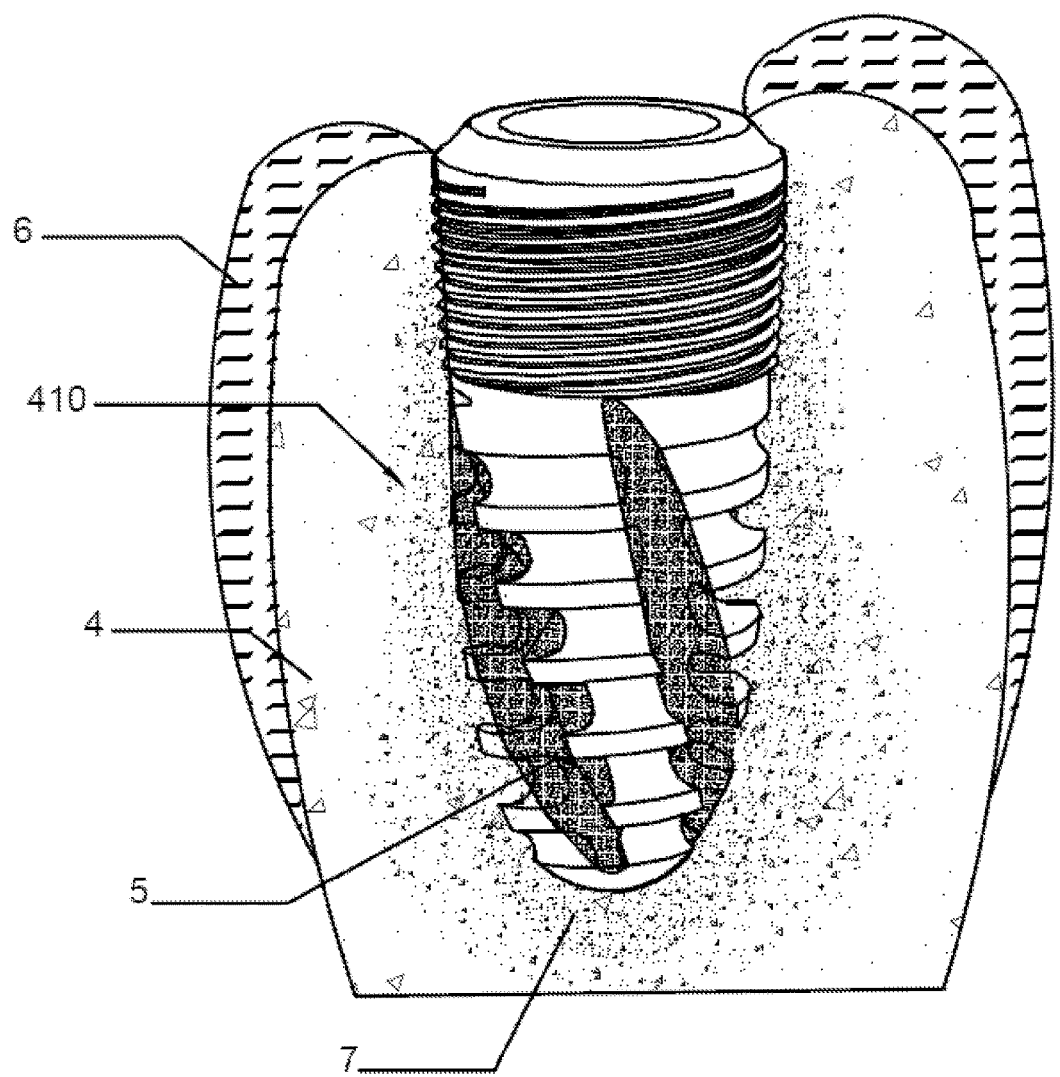
FIG. 22 is a view of the implant of FIG. 19 inserted into a jawbone, and illustrating how the bone shavings of cutting edges accumulate and condense in the vertical channels and next to the implant.
Figure 23:
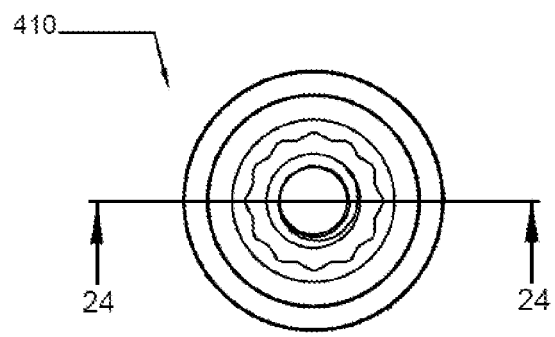
FIG. 23 is a top view of the implant of FIG. 19.
Figure 24:
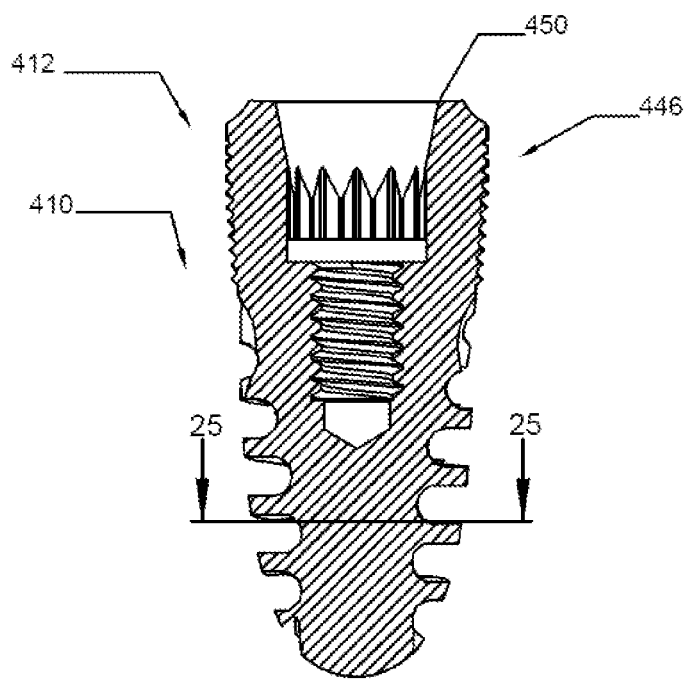
FIG. 24 is a cross-sectional view taken generally along line 24-24 of FIG. 23.

In a particularly preferred embodiment, as illustrated, multiple channels 432 are formed in the implant 410 in spaced relation to one another. For example, as illustrated in FIGS. 22 and 25, the implant 410 has four channels 432 formed therein, each having a non-rectilinear pathway generally opposite the spiral thread of the osteotomy blade and sized and configured so as to receive shaved and cut bone fragments therein during the installation of the implant 410. This is the self grafting feature of this implant as it derives and condenses the bone shavings of osteotomy blades through vertical channels 432 and against the core 414. This is beneficial as the osseointegration of the implant 410 is further assisted by having the channels 432 extend across many planes or outer surfaces of the implant 410 so as to more firmly hold the implant 410 in place when osseointegration occurs. It can be seen in FIGS. 19 and 25 that the channels 432 extend generally in the apical part of the in-bone portion of implant 410 from the neck 446 to the tip 416. Thus, osseointegration will occur at many points surrounding the in-bone portion of the implant 410.

As illustrated in FIG. 25, the formation of the one or more channels 432 into the spiral thread or osteotomy blade is done at a non-normal angle with respect to the core body. In other words, the one or more channels 432 are formed at an angle of less than ninety degrees, such as approximately thirty degrees, such that one edge 424 of the side of the channel or exposed edges of the osteotomy blades 418 have a bone cutting edge, while the generally opposite side or wall of the channel 432, and the exposed edges 425 of the threaded spiral or osteotomy blade are not bone cutting. In the examples illustrated, the spiral thread has a generally clockwise direction, whereas the open-faced channels 432 have a generally opposite or counter-clockwise orientation and direction. Thus, the exposed edges 424 at the right side of the channel 432 are bone-cutting edges, whereas the exposed edges 425 on the left side of the channel are not bone cutting edges. This enables the implant 410 to be drivenly rotated in a clockwise manner and cut and carve bone as it is drivenly rotated into the patient's bone. However, due to the non-cutting edge at the opposite side of the channels, reverse movement of the implant 410 is restricted or even prevented Similar to that described above, an outermost or peripheral edge or surface of the osteotomy blade thread is generally flat so as to form a stabilizing wall 434. This stabilizing wall has the same features and advantages as that described above, in that it provides a substantially large area boundary between the implant 410 and the adjacent bone so as to provide horizontal or lateral stabilization of the implant 410 with respect to the adjacent bone.

As can be seen in FIG. 25 the cross-section of the osteotomy blade thread 418 is generally frustoconical. One or more cutting edges 424 are formed by the osteotomy blade thread 418, and more particularly defined by the stabilizing wall 434. These bone cutting edges can comprise the exposed leading edges formed by the channels 432, and may also comprise the upper and lower edges formed by the upper and lower surfaces 420 and 422 of the osteotomy blade thread. These edges are sufficiently sharp so as to cut directly into the bone as the implant 410 is rotated and driven into the bone, essentially carving the bone where the osteotomy blade thread 418 will reside within the bone, or in other words creating a self-osteotomy, which essentially corresponds to the configuration of the in-bone portion of the implant 410.

The upper surface 420 and lower surface 422 of the osteotomy blade thread may include ramps and grooves, as described above, in order to further facilitate the direction of cut bone shavings. However, as illustrated, these upper and lower surfaces 420 and 422 may be generally rounded or flat and not include such ramps or channeling grooves.

With reference again to FIG. 20, in an embodiment of the present invention, an upper portion, also referred to herein as a coronal media portion, of the implant is blasted with media, such as sand or other particles, so as to create divots, imperfections and otherwise roughen the surface for better osseointegration. Such roughened surface, illustrated by cross-hatching and the reference number 452, allows the bone to better adhere to the outer surface of the media blasted portion of the implant. However, a lower portion 454 of the implant, also referred to herein as an apical portion, is not media blasted and roughened, but instead is left with its machined finished surface. The machined finished surface has sharp edges, which are used to cut into and carve into the bone. Media finishing or roughing the entire implant would dull these sharp cutting edges. Thus, typically, the majority of the cutting blades portion of the implant is not media blasted, wherein an upper portion, including the neck and head of the implant, is media blasted to roughen the surface for better osseointegration.

As illustrated in FIG. 21, in an embodiment of the present invention the neck portion includes microthreads 456. These microthreads have, as illustrated, have the same outer diameter. For the microthreads that are on the lower portion of the tapered implant, these microthreads have a greater width or thickness than those of the upper portion. As shown in FIG. 21 by the areas having arrows a and b pointing thereto, the microthreads have the same pitch angle as the major blades of the implant, which are not normal or at a ninety degree angle with respect to the central axis of the implant.

Figure 26:
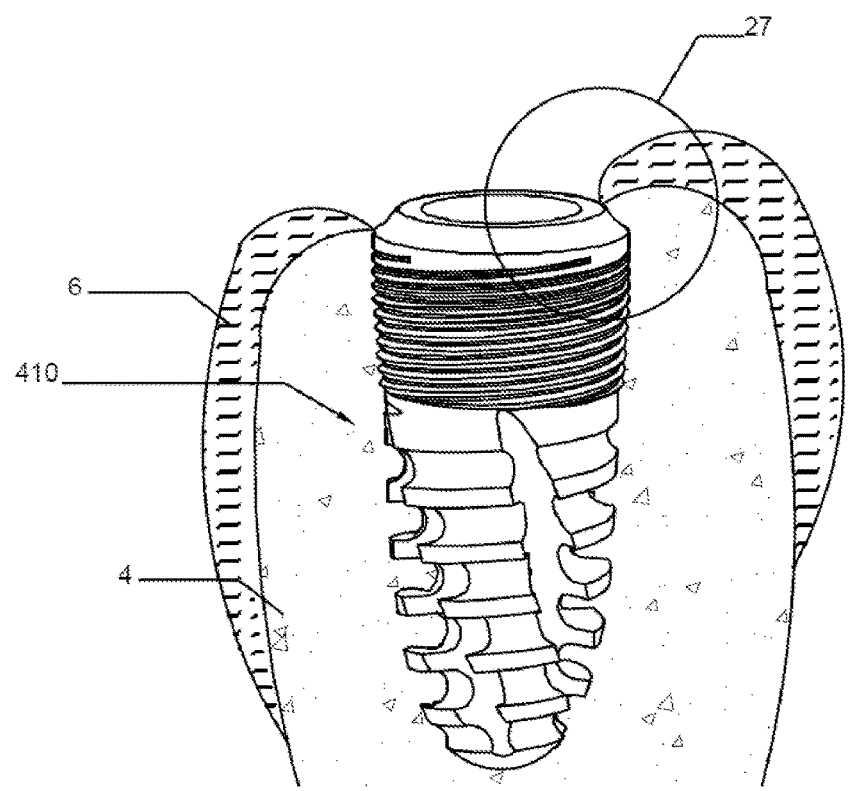
FIG. 26 is a partially sectioned diagrammatic view illustrating the bone implant of FIG. 19 installed in a jaw of a patient.

With reference now to FIG. 26, in order to install the implant 410 into the bone, such as a patient's jawbone when attaching a dental restoration, a pilot hole is first drilled into the bone, as illustrated and described above with respect to FIG. 13. The tip 416 corresponds to the diameter of the drilled pilot hole, typically being slightly smaller than the diameter of the pilot hole so as to be received therein. The pilot hole guides the placement of the implant 410 into the bone 4. Typically, the pilot hole 8 is approximately the length of the in-bone portion of the implant 410, in the case of FIG. 26 being from the top surface 450 to the tip 416. While the pilot hole 8 is used to generally guide the placement of the implant 410, it will be understood by those skilled in the art that it is in fact the osteotomy blade and thread 418 which create the self-osteotomy and carve the bone 4 as the implant 410 is installed.

In prior implants, the size of the increasing pilot hole or osteotomy drilled before the insertion of the implant, as a diameter, was slightly less than the outer diameter of the at least threaded portion of the implant. This created a very tight fit with pressure in an effort to keep the implant within the patient's bone, such as jawbone. However, this pressure created bone pain, and sometimes failure of the implant, as indicated above. However, in the present invention, as the implant creates its own osteotomy with the cutting edges of the osteotomy blades essentially carving out the bone so that the in-bone portion of the implant resides in the carved out portion, the actual diameter of the osteotomy itself is much smaller than previously, and approximates the diameter of the core body instead of the threads or overall implant. However, there is no bone pressure as the implant is carved into the bone to create its own self-osteotomy mirroring that of the configuration of the in-bone portion of the implant 410 itself.

In a particularly preferred embodiment, the bone implant 410 comprises a dental implant whose head 412 is adapted to receive an abutment, such as through recess 436. Exemplary abutments and dental restorations are described above with respect to FIGS. 10 and 11, or could be those used commonly in the art. Although not illustrated, in FIG. 26 it will be appreciated that the abutment and false tooth or dental restoration will be somewhat obscured by the gum tissue 6 extending upwardly from the jawbone 4, so as to give the appearance of a natural tooth of the patient.

Figure 27:
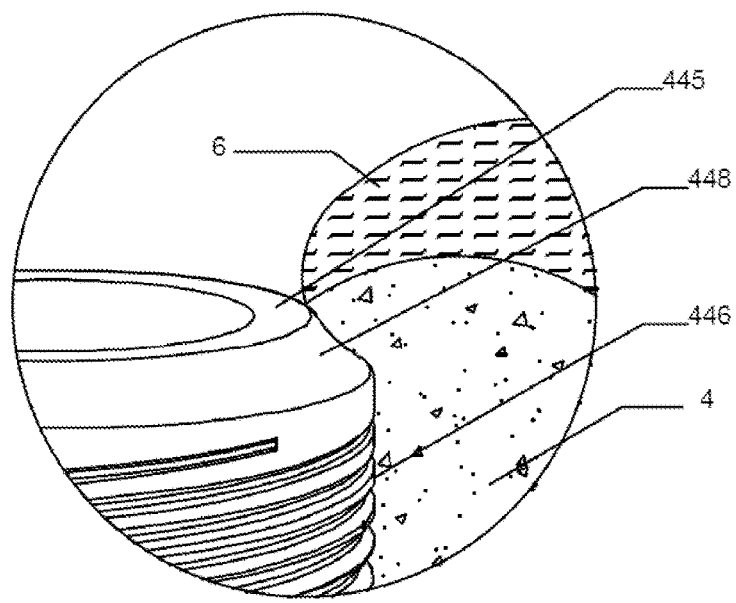
FIG. 27 is an enlarged partially sectioned view taken from FIG. 26, illustrating how the concave top of the bone level implant encourages bone to grow over the implant, further securing the implant in place.

In the embodiment illustrated in FIG. 27, the portion 448 between the upper surface 450 of the generally cylindrical neck portion 446 is concave, as illustrated, which allows taking advantage of the maximum alveolar crest bone available as the implant may be placed at or below the highest part of the cortical bone, so as to accommodate invariable unevenness of the alveolar crest bone. This feature also allows bone to grow over the concave area 448, further securing the implant in place.

Figure 28:
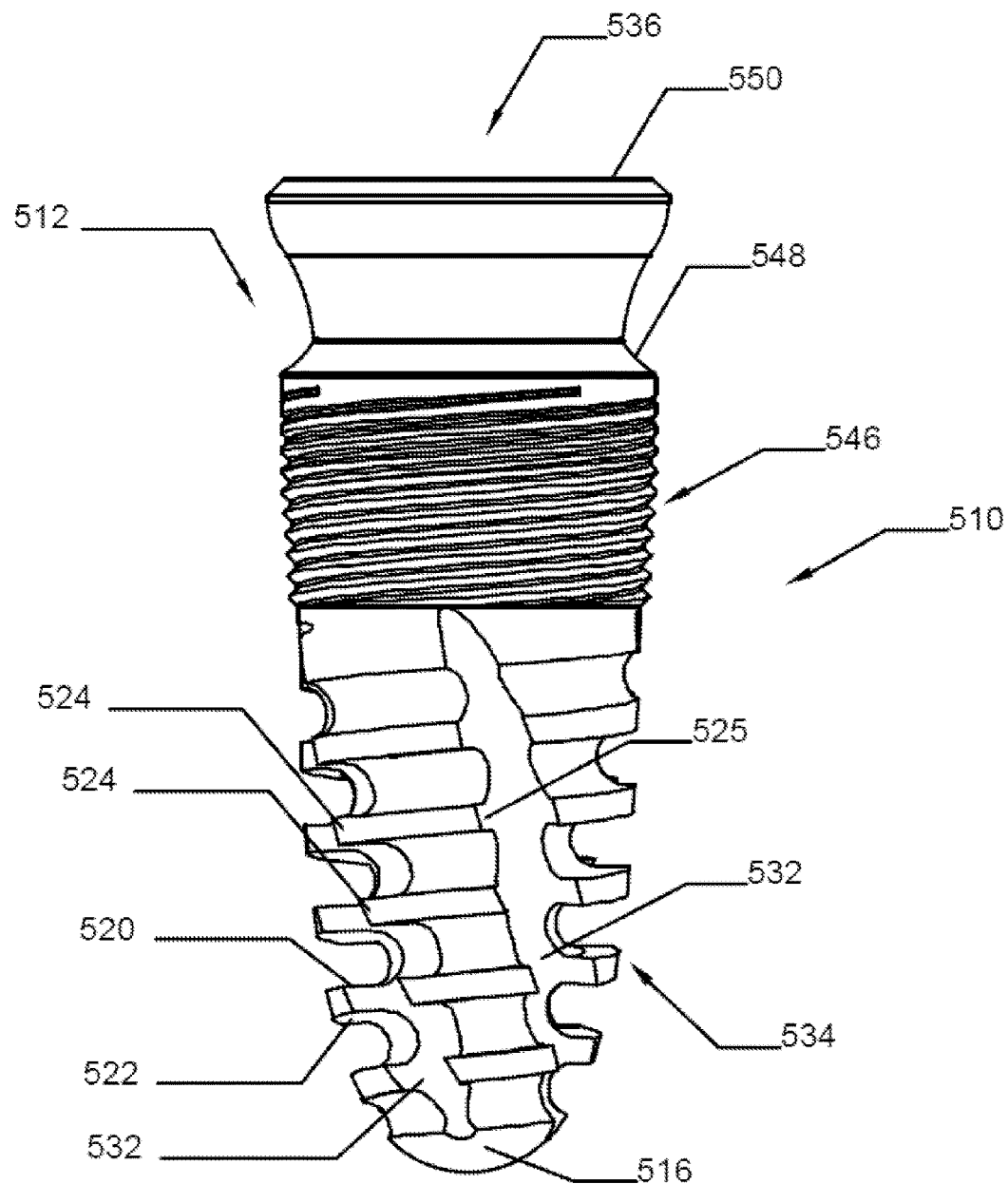
FIG. 28 is a front perspective view of a tissue level bone implant embodying the present invention.
Figure 29:
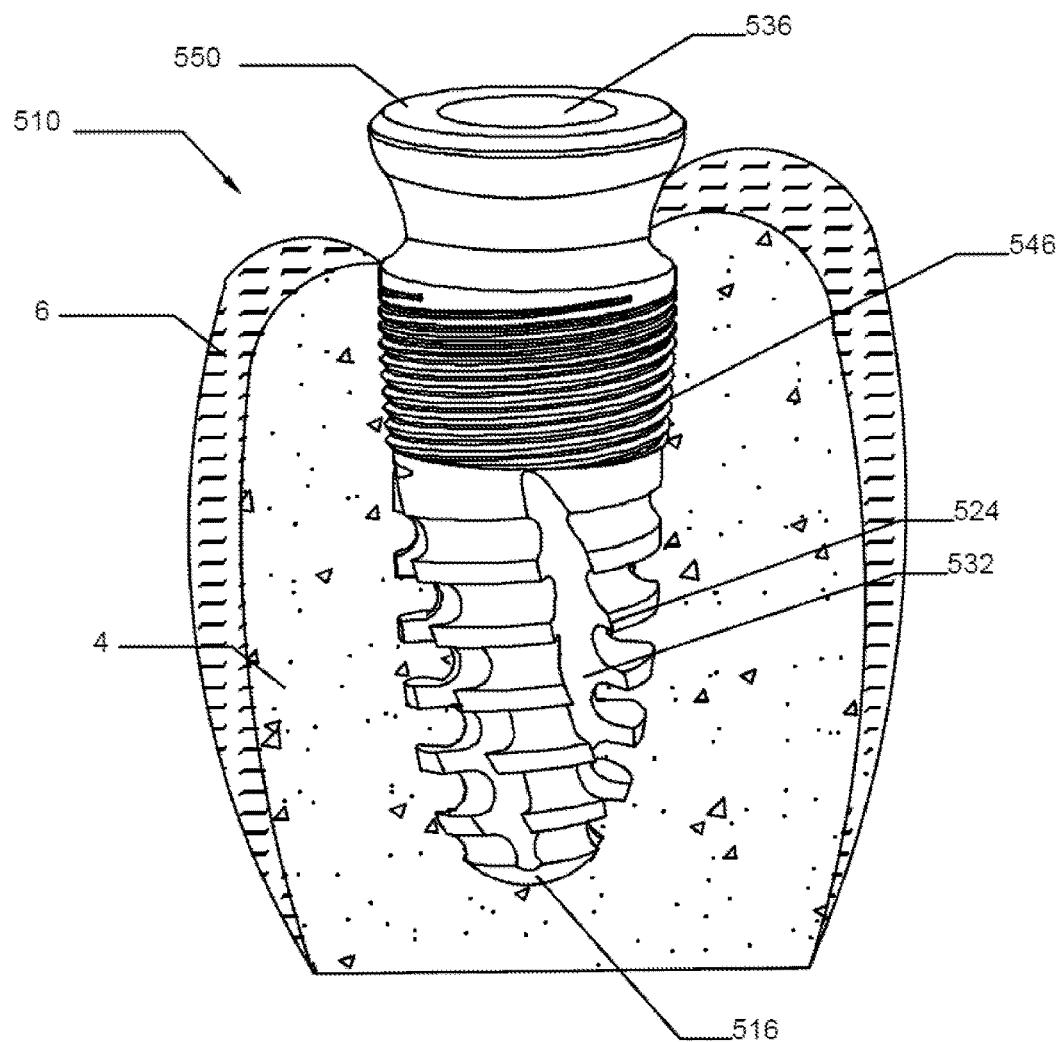
FIG. 29 is a partially sectioned view illustrating the implant of FIG. 26 installed in a patient's jaw.

With reference now to FIGS. 28 and 29, a tissue level dental implant 510 is shown with the head 512 extending through the soft tissue and into oral environment. The concave 448 surface of implant 410 is merged in this tissue level implant with the head 512. Otherwise this tissue level implant has the same components and features described above with respect to FIGS. 19-27, but labeled with a "500" instead of a "400" reference numeral. As such, the implant 510 includes a head 512 having a core body 514 extending to a tip 516, with an osteotomy blade 518 forming a spiral thread along a length thereof, as illustrated. The thread 518 includes a stabilizing wall 534 having a bone cutting edge 524, and upper and lower surfaces 520 and 522. One or more channels 532 are formed in the implant 510, and particularly through the osteotomy blade thread 518 and in-bone portion, as illustrated between the cylindrical neck portion 546 to tip 516.

This implant is what is known as a tissue level dental implant in that the neck portion is extended and has a generally inwardly curved or beveled portion 552 which substantially corresponds with the gingival tissue of the patient's mouth, as illustrated in FIG. 29.

Thus, as illustrated in FIG. 29, the lower cylindrical neck portion 546 is typically disposed within the bone 4, while the intermediate portion 552 extends above the lowest portion of the bone and corresponds to at least a portion of the gingival or gum tissue 6. A generally concave portion 548 may still be formed between the neck 546 and the upper surface 550, as illustrated, so as to accommodate unevenness of the bone and gum tissue extending thereon. Means, such as the illustrated recess 536, for receiving and attaching a dental abutment is also provided.

Figure 30:
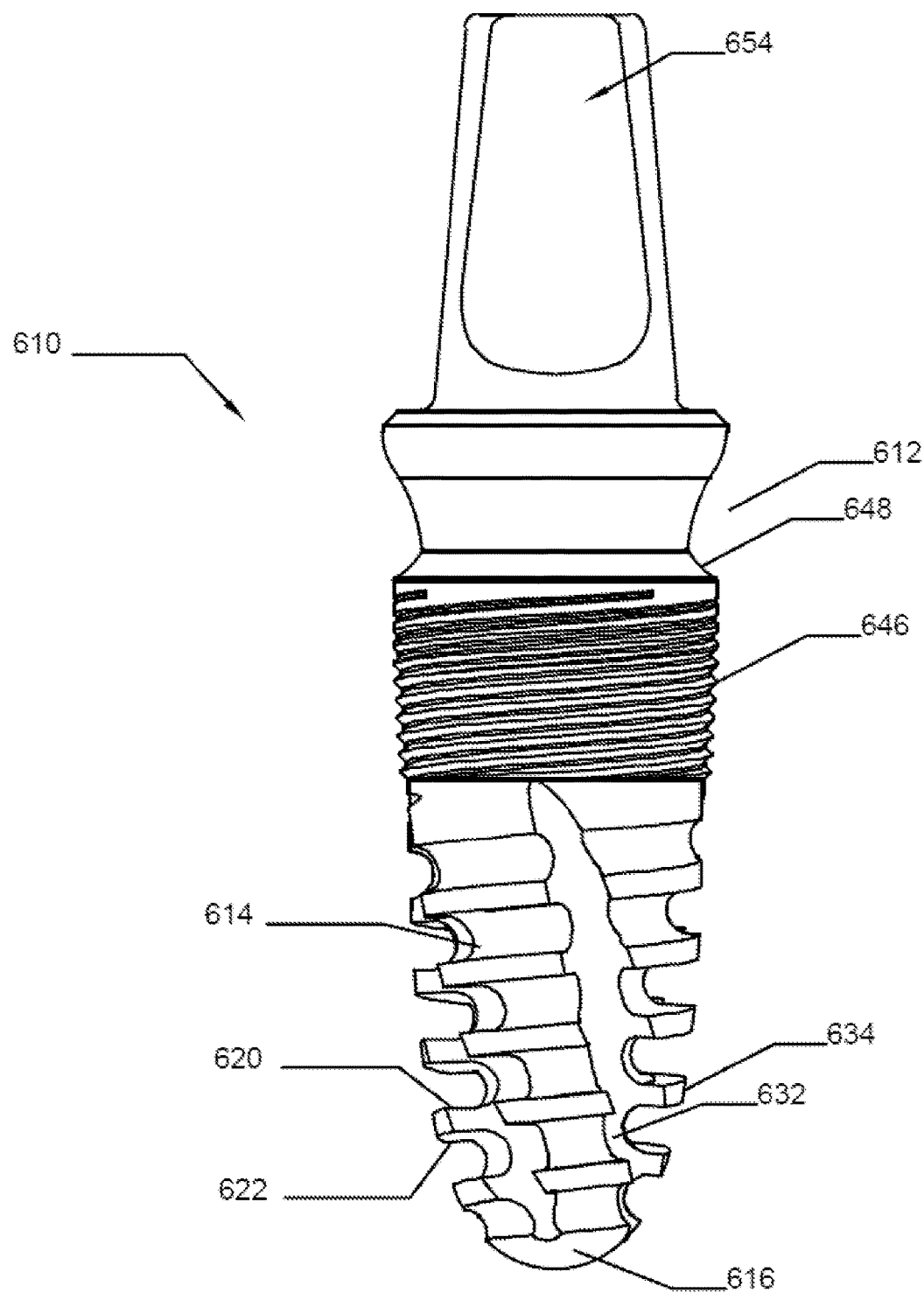
FIG. 30 is a front perspective view of a one piece implant embodying the present invention.
Figure 31:
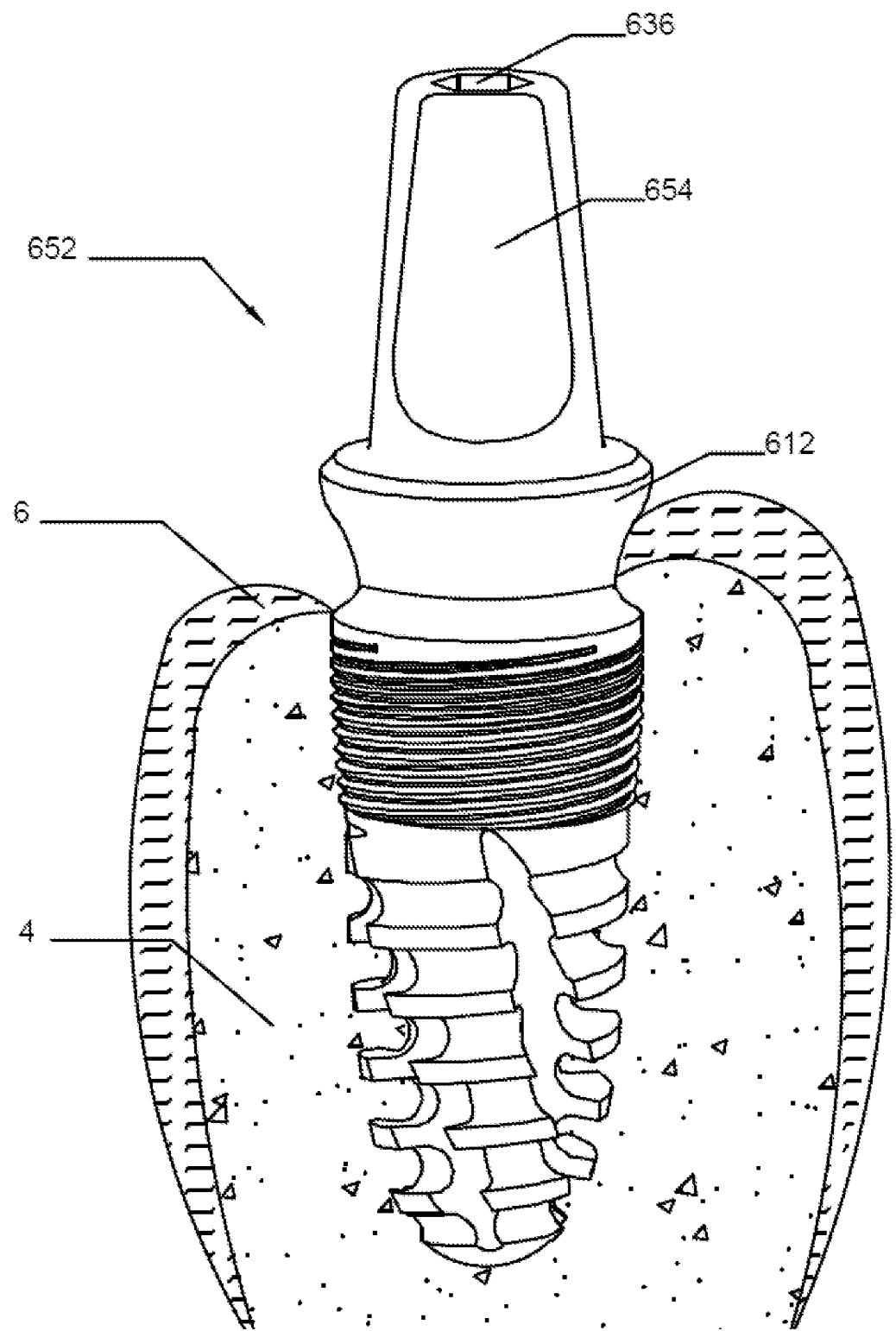
FIG. 31 is a partially sectioned view illustrating the implant of FIG. 28 installed in a patient's jaw.

With reference now to FIGS. 30 and 31, yet another implant 610 embodying the present invention is shown. Many features and components of this implant 610 correspond with the implant illustrated and described above with respect to FIGS. 19-27, but are labeled with a "600" reference number as opposed to a "400" reference number. As such, the implant 610 includes a head 612, a core body 614 extending to a tip 616. The osteotomy blade thread includes a stabilizing wall 634 having one or more bone cutting edges 624, and upper and lower surfaces 620 and 622. One or more open-faced channels 632 extend through the multiple turns of the osteotomy blade spiral thread 618. In this case, the channels 632 extend into the neck portion 646 and down into the tip 616.

With particular reference to FIG. 30, this dental implant 610 is referred to as an all-in-one, wherein the head 612 includes an abutment 652 which extends above the gingival surface into the oral cavity so that to receive a clinical crown.

The implant 610 includes a platform 656 which is the same part as top surface 550, which may rest at the level of gum tissue 4 and which acts as a seat to a portion of the crown, as illustrated in FIG. 31. A recess 636 may or may not be used to rotate the abutment in place.

Figure 32:
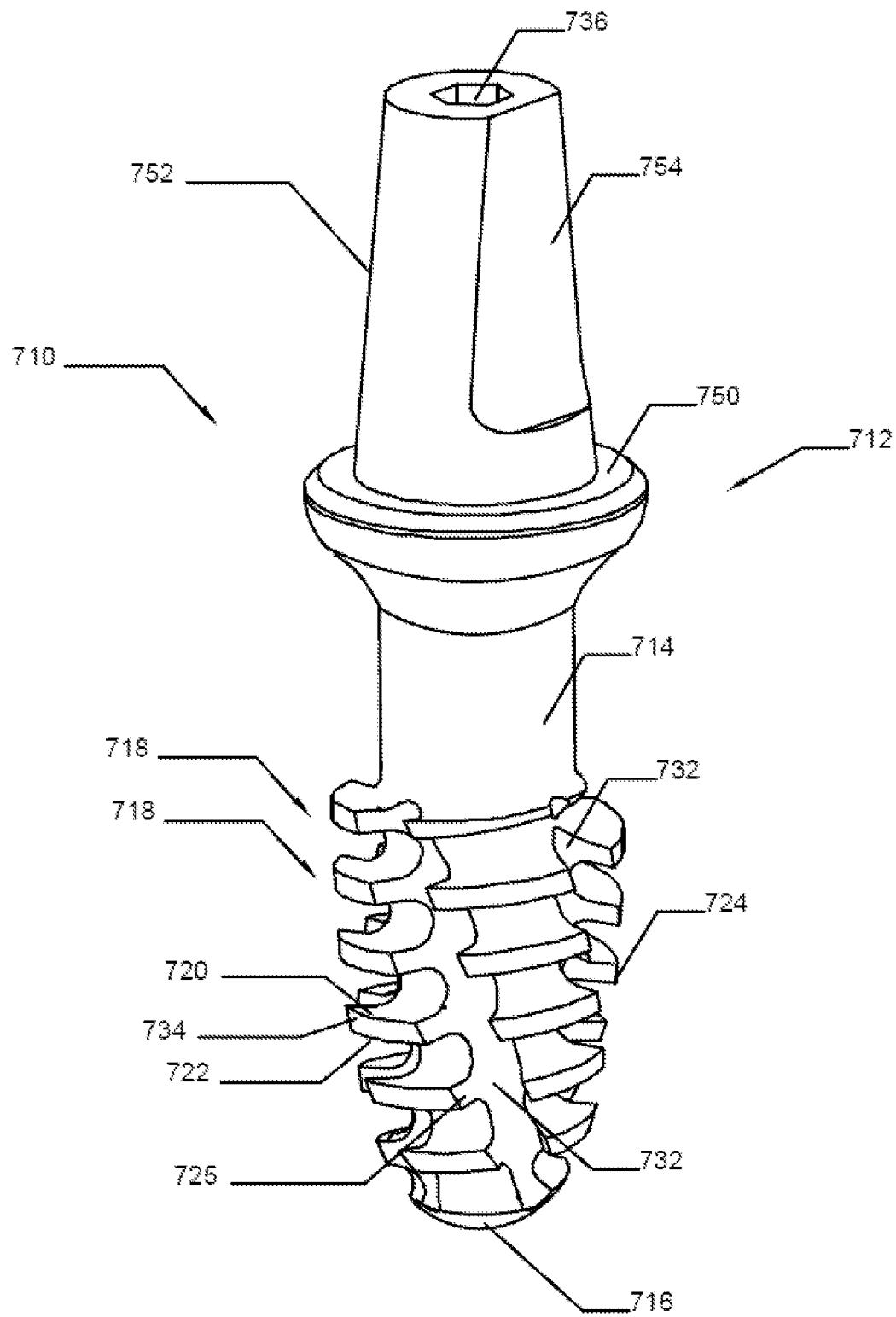
FIG. 32 is a front perspective view of a trans-cortical implant embodying the present invention.
Figure 33:
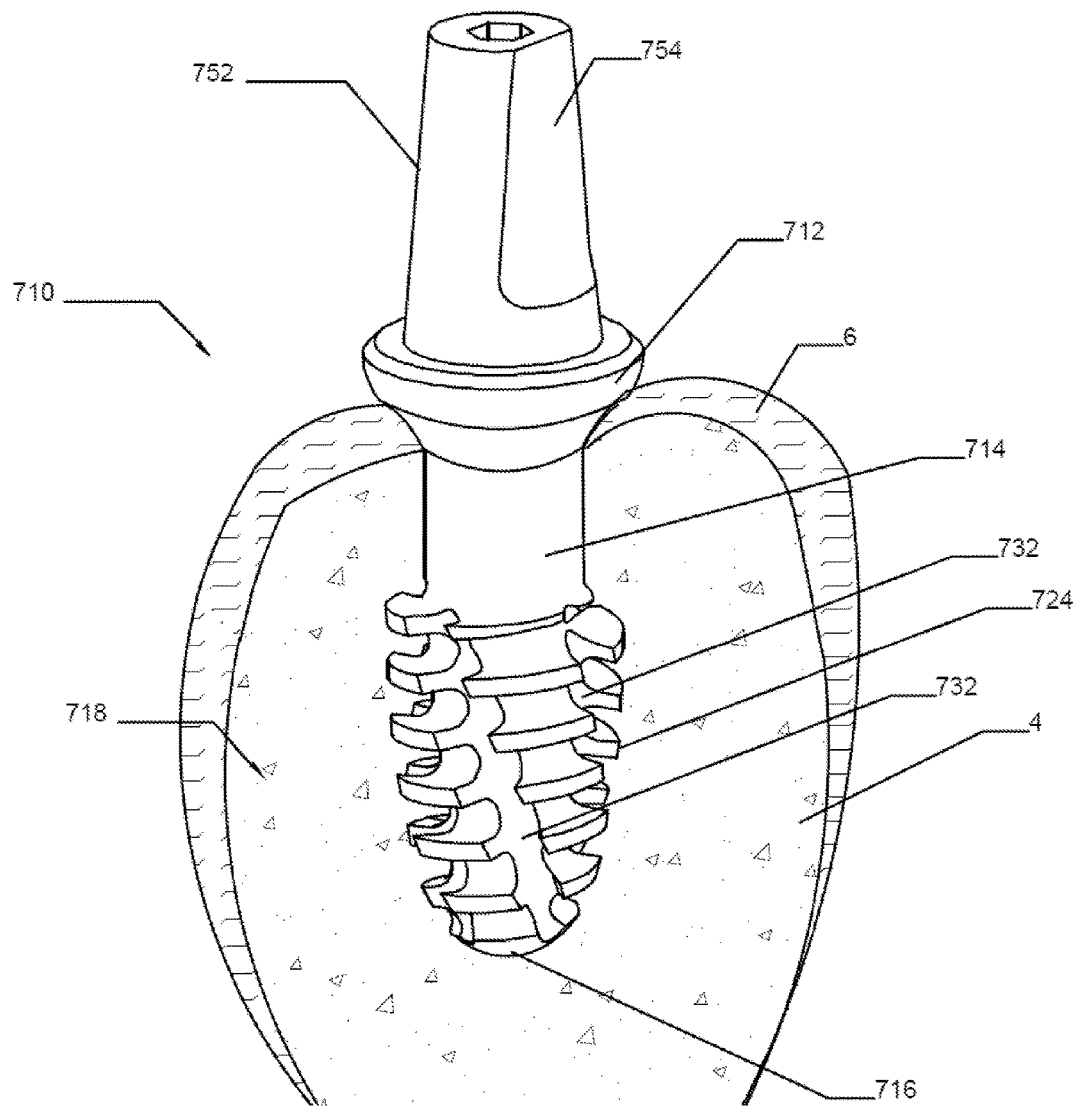
FIG. 33 is a partially sectioned diagrammatic view illustrating the implant of FIG. 32 installed in a patient's jaw.

With reference now to FIGS. 32 and 33, yet another implant 710 is shown having many of the same characteristics, components, features, etc. as the implants described above with respect to FIGS. 19-27, but labeled with reference numbers in the "700s". As such, the implant 710 includes a head 712 having a core body 714 which extends to a tip 716. An osteotomy blade spiral thread 716 extends along at least a portion of the implant 710, in this case a lower portion, to the tip 716. Channels 732 are formed in the osteotomy blade 718, as described above. An outer peripheral surface is generally flat so as to form a stabilizing wall 734, and the osteotomy blade 718 includes at least one bone cutting edge 724. Upper and lower surfaces 720 and 722 of the osteotomy blade 718 may vary in configuration, as noted above. The cross-sectional thickness of the osteotomy blade thread 718 may increase from the uppermost portion towards the tip 716. This is for the same reasons and benefits as described above.

With continued reference to FIGS. 32 and 33, this dental implant 710 is generally referred to as a trans-cortical implant in that a generally cylindrical shaft portion of the core body 714 extends into the bone 6 and the head 712 including the abutment 752 resides above the bone and into the gingival tissue 4. A platform 750 and a generally conical upper head portion having a bevel 754 may be used for receiving a crown. A recess 736 may or may not be used in order to rotate the implant in place and provide anti-rotational resistance for the restoration.

With reference now to FIGS. 34-37, bone implants similar to that described above with respect to FIGS. 16-18 are illustrated. The embodiments having the osteotomy blade spiral thread and open-face channels of FIGS. 19-27 are not necessarily limited to dental implants. These features and advantages can also be advantageously used in other bone implant and fastening circumstances, such as orthopedic applications.

Figures 34, 35:
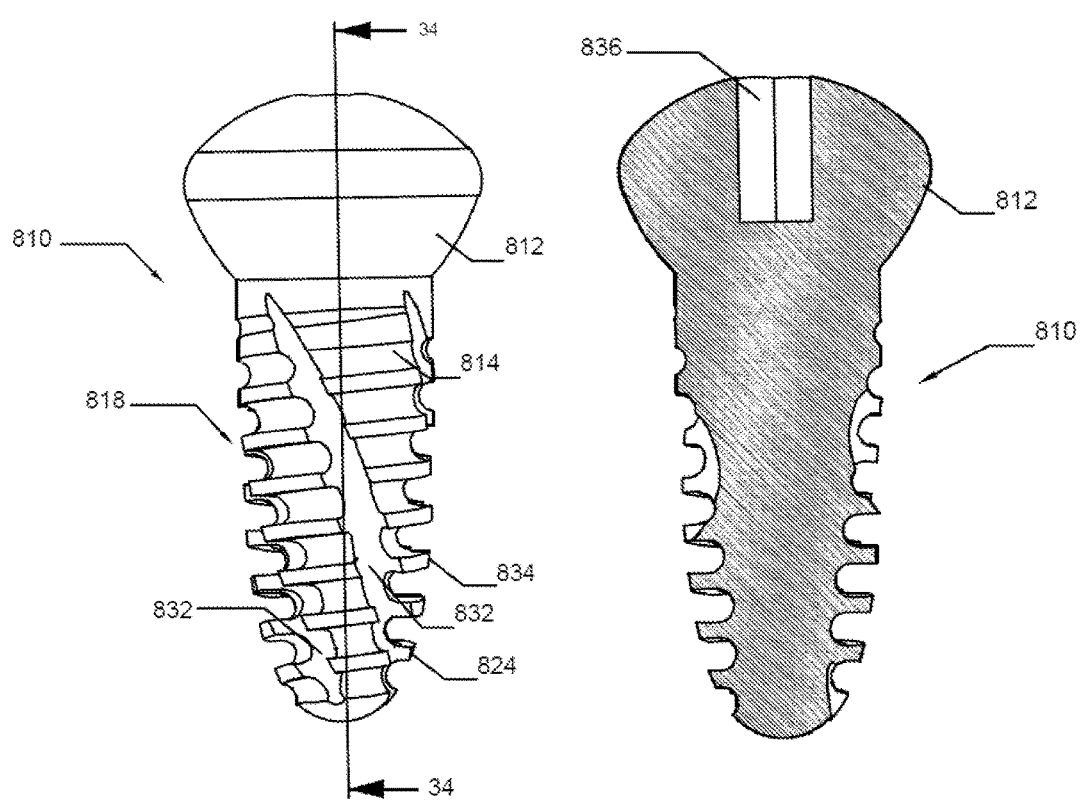
FIG. 34 is a front perspective view of a orthopedic bone implant embodying the present invention.
FIG. 35 is a partially sectioned diagrammatic view taken generally along line 35-35 of FIG. 34.

With particular reference to FIG. 34, a bone implant 810 has a head 812, which is illustrated as being conical but may also be flat. It will be understood that the head 812 will have a slot or recess 836 for a driver to drive the bone implant 810 into the bone.

The bone implant 810 includes a core body 814 extending to a tip 816. An osteotomy blade 818 extends as a spiral thread towards the tip 816. The spiral thread has upper and lower surfaces 820 and 822, and an outer peripheral edge is generally flat to form a stabilizing wall 834, as described above. The osteotomy blade 818 includes one or more bone cutting edges 824, such as at the edge of the stabilizing wall 834 defined by the open-faced channels 832 formed in the implant 810. Although a rounded tip 816 is illustrated in FIG. 34, it will also be understood that the tip 816 could present as a sharpened point so as to be driven into bone, such as during surgical operations to fasten pieces of bone to one another, plates, devices, and the like to bones, etc.

Figures 36, 37:
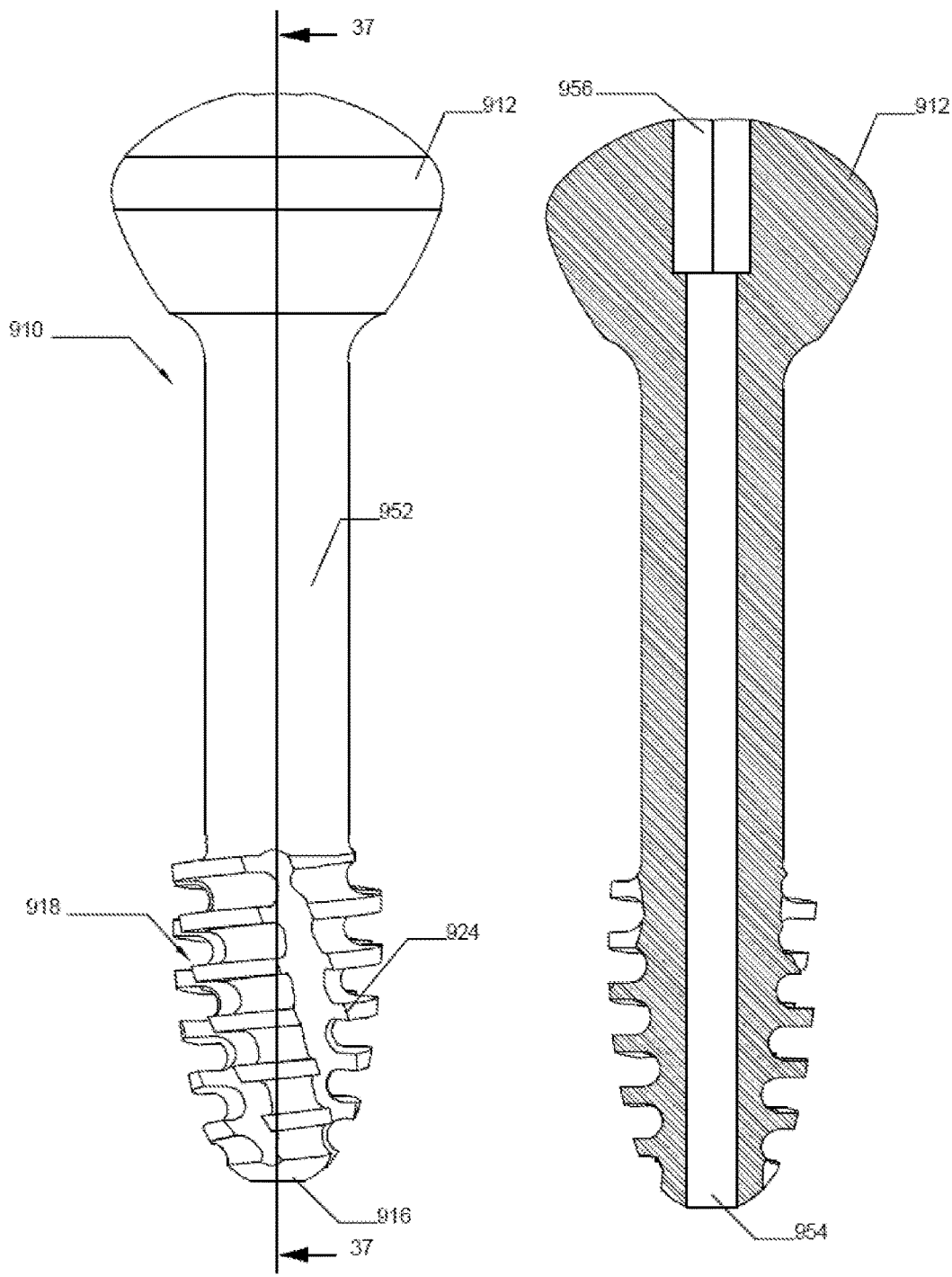
FIG. 36 is a front perspective view of another orthopedic bone implant embodying the present invention.
FIG. 37 is a cross-sectional view taken generally along line 37-37 of FIG. 36.

With reference now to FIGS. 36 and 37, yet another bone implant 910 is illustrated for use in non-dental implant applications. In this case, there is an unthreaded portion 952 of the shaft between the head 912 and the tip 916. As such, the osteotomy blade thread 918 extends only partially along the core body 952 of the implant 910. This may be useful, for example, when attaching a plate or other device to a bone, wherein the lower portion containing the osteotomy blade thread 918 is inserted into the bone and the non-threaded portion 952 extends through the plate, etc. The osteotomy blade 918 includes a generally flat stabilizing wall 934 at the peripheral edge or surface thereof, which defines a bone cutting edge 924. One or more open-faced channels 932 are formed in the osteotomy blade thread 918. FIG. 37 is a cross-sectional view taken generally along line 37-37 of FIG. 36, illustrating a passageway 954 formed through the implant 910 to serve various purposes of the surgeon. A recess 956 in the head 912 may be used to drive the implant 910. Once again, the tip 916 may be rounded or come to a sharp point as needed.

The non-dental applications of the bone implant of the present invention, as illustrated in FIGS. 34-37, still have the same advantages as the dental implant embodiments, in that the osteotomy blade is responsible for gradual and unmatchable perfect self-osteotomization. The stabilizing walls provide stabilization of the implant, and the channels collect bone fragments and tissue and allow fluid and blood transfer between adjacent sections of bone and the bone shavings, and promote the subsequent growth of blood vessels and new bone into the channels.

In the past, and particularly in dental implant applications, certain metals and metal alloys were preferable to others as the metal or metal alloys were able to allow micro-integration of bone at its surfaces. For example, titanium allows micro-integration of bone due to its irregular or porous surface. Zirconium as a material has certain benefits, but typically is not possible to use in implants as sufficient micro-osseointegration does not form at the metal's surfaces. However, the configuration and design of the present invention allows dental implants and bone screws and the like to be comprised of zirconium and other metals which previously were not possible as the present invention creates and relies primarily upon macro-osseointegration as opposed to micro-osseointegration. The macro-osseointegration, as described above, is due to the use of the autogenous biological materials, including the carved bone, into the channels, allowing fluid and blood transfer and flow into these areas such that the bone integrates within a relatively short period of time. Of course, with certain metal materials a level of micro-osseointegration will occur in the present invention as well.

Although several embodiments have been described in detail for purposes of illustration, various modifications may be made without departing from the scope and spirit of the invention. Accordingly, the invention is not to be limited, except as by the appended claims.

What is claimed is:

1. A self-osteotomizing bone implant comprising:
a head configured to receive a dental abutment, wherein the head comprises an upper surface and a neck portion extending therefrom, wherein the neck portion is substantially cylindrical in shape, wherein the head is configured to be placed at or below an upper bone surface;
a core body extending from the neck portion of the head to a tip generally opposite the head;
an osteotomy blade extending outwardly from at least a majority of a length of the core body and forming a spiral thread having multiple turns around the core body, wherein at least a portion of a surface of the osteotomy blade distal and facing outwardly from the core body is generally flat and defines a stabilizing wall having a bone cutting edge, wherein an outer diameter of the osteotomy blade extending outwardly from the core body progressively decreases in the direction from the head to the tip to provide a tapered configuration thereto, wherein a radius of the osteotomy blade progressively narrows proximate to the bone cutting edge; and
at least one non-rectilinear channel extending a length of the implant so as to pass through multiple turns of the osteotomy blade, wherein the at least one channel is formed in the osteotomy blade and extends from an outer edge of the osteotomy blade to at least the core body, wherein the at least one channel is formed at an angle of less than 90 degrees with respect to the core body so as to create a bone cutting edge on the osteotomy blade on one side of the channel and a non-cutting edge on the osteotomy blade on the generally opposite side of the channel, wherein the at least one channel is oriented in a direction generally opposite of the spiral thread of the osteotomy blade and configured to receive bone shavings cut by the osteotomy blade during implantation of the implant into bone and direct the bone shavings towards the tip of the implant.

2. The implant of claim 1, wherein the at least one channel is open-faced.

3. The implant of claim 1, further comprising a plurality of non-rectilinear channels, wherein the plurality of non-rectilinear channels is disposed in spaced relation to one another.

4. The implant of claim 1, wherein the at least one channel is generally spiral in shape.

5. The implant of claim 1, wherein the at least one channel extends from an outer edge of the osteotomy blade into the core body.

6. The implant of claim 1, wherein the at least one channel extends from the head to the tip of the implant.

7. The implant of claim 1, wherein the at least one channel extends from the neck portion to the tip of the implant.

8. The implant of claim 1, wherein the at least one channel is formed at an angle of approximately 30 degrees with respect to the core body.

9. The implant of claim 1, wherein the tip is generally rounded in shape.

10. The implant of claim 9, wherein the tip is shaped to correspond to the shape of pilot hole drilled in the bone prior to implantation of the implant thereto.

11. The implant of claim 1, wherein the neck portion further comprises a plurality of microthreads formed thereon, wherein the plurality of microthreads have a pitch angle generally corresponding to a pitch angle of the osteotomy blade.

12. The implant of claim 1, wherein head further comprises a generally concave depression between the upper surface and the neck portion, wherein the concave depression is configured to receive bone therein when the implant is implanted.

13. The implant of claim 1, wherein an outer diameter of the core body progressively decreases in the direction from the head to the tip.

14. The implant of claim 1, wherein an upper portion of the implant is roughened by media blasting and a lower portion of the implant comprising at least the tip has a smoother finish than the upper portion.

15. A self-osteotomizing bone implant comprising:
a head configured to receive a dental abutment, wherein the head comprises an upper surface and a neck portion extending therefrom, wherein the neck portion is substantially cylindrical in shape, wherein the head is configured to be placed at or below an upper bone surface;
a core body extending from the neck portion of the head to a tip generally opposite the head;
an osteotomy blade extending outwardly from at least a majority of a length of the core body and forming a spiral thread having multiple turns around the core body, wherein at least a portion of a surface of the osteotomy blade distal and facing outwardly from the core body is generally flat and defines a stabilizing wall having a bone cutting edge, wherein an outer diameter of the osteotomy blade extending outwardly from the core body progressively decreases in the direction from the head to the tip to provide a tapered configuration thereto, wherein a radius of the osteotomy blade progressively narrows proximate to the bone cutting edge; and
a plurality of channels extending a length of the implant so as to pass through multiple turns of the osteotomy blade, wherein each of the plurality of channels is formed in the osteotomy blade and extends from an outer edge of the osteotomy blade to at least the core body, wherein each of the plurality of channels is formed at an angle of less than 90 degrees with respect to the core body so as to create a bone cutting edge on the osteotomy blade on one side of each respective channel and a non-cutting edge on the osteotomy blade on the generally opposite side of each respective channel, wherein each of the plurality of channels is oriented in a direction generally opposite of the spiral thread of the osteotomy blade and configured to receive bone shavings cut by the osteotomy blade during implantation of the implant into bone and direct the bone shavings towards the tip of the implant.

16. The implant of claim 15, wherein each of the plurality of channels is generally spiral in shape.

17. The implant of claim 15, wherein at least one channel extends from an outer edge of the osteotomy blade into the core body.

18. The implant of claim 15, wherein at least one channel extends from the head to the tip of the implant.

19. The implant of claim 15, wherein at least one channel extends from the neck portion to the tip of the implant.

20. The implant of claim 15, wherein at least one channel is formed at an angle of approximately 30 degrees with respect to the core body.

21. The implant of claim 15, wherein the tip is generally rounded in shape.

22. The implant of claim 21, wherein the tip is shaped to correspond to the shape of pilot hole drilled in the bone prior to implantation of the implant thereto.

23. The implant of claim 15, wherein the neck portion further comprises a plurality of microthreads formed thereon, wherein the plurality of microthreads have a pitch angle generally corresponding to a pitch angle of the osteotomy blade.

24. The implant of claim 15, wherein head further comprises a generally concave depression between the upper surface and the neck portion, wherein the concave depression is configured to receive bone therein when the implant is implanted.

25. The implant of claim 15, wherein an outer diameter of the core body progressively decreases in the direction from the head to the tip.

26. The implant of claim 15, wherein an upper portion of the implant is roughened by media blasting and a lower portion of the implant comprising at least the tip has a smoother finish than the upper portion.

* * * * *